US011046972B2

(12) United States Patent
Narva et al.

(10) Patent No.: US 11,046,972 B2
(45) Date of Patent: Jun. 29, 2021

(54) NUCLEIC ACID MOLECULES TO CONTROL INSECT PESTS

(71) Applicants: Dow AgroSciences LLC, Indianapolis, IN (US); Fraunhofer-Gesellschaft zur Förderung der angewandten Forschung e. V., Munich (DE)

(72) Inventors: Kenneth E. Narva, Zionsville, IN (US); Sarah E. Worden, Indianapolis, IN (US); Meghan Frey, Greenwood, IN (US); Murugesan Rangasamy, Zionsville, IN (US); Premchand Gandra, Indianapolis, IN (US); Wendy Lo, Indianapolis, IN (US); Elane Fishilevich, Indianapolis, IN (US); Andreas Vilcinskas, Giessen (DE); Eileen Knorr, Gießen (DE)

(73) Assignees: Dow AgroSciences LLC, Indianapolis, IN (US); Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 7 days.

(21) Appl. No.: 15/166,623

(22) Filed: May 27, 2016

(65) Prior Publication Data
US 2017/0022518 A1    Jan. 26, 2017

Related U.S. Application Data

(60) Provisional application No. 62/168,606, filed on May 29, 2015.

(51) Int. Cl.
| | | |
|---|---|---|
| *C12N 15/82* | (2006.01) |
| *C12N 15/113* | (2010.01) |
| *C07K 14/435* | (2006.01) |
| *A01N 57/16* | (2006.01) |
| *C07K 14/325* | (2006.01) |
| *C12Q 1/6895* | (2018.01) |

(52) U.S. Cl.
CPC ......... *C12N 15/8286* (2013.01); *A01N 57/16* (2013.01); *C07K 14/325* (2013.01); *C07K 14/43563* (2013.01); *C12N 15/113* (2013.01); *C12N 15/8218* (2013.01); *C12Q 1/6895* (2013.01); *C12N 2310/14* (2013.01); *C12Q 2600/13* (2013.01); *C12Q 2600/158* (2013.01); *C12Q 2600/178* (2013.01); *Y02A 40/146* (2018.01)

(58) Field of Classification Search
CPC .................................................. C12N 15/8286
USPC ....................................................... 800/285
See application file for complete search history.

(56) References Cited

U.S. PATENT DOCUMENTS

| | | |
|---|---|---|
| 2007/0050860 A1 | 3/2007 | Andersen et al. |
| 2010/0192265 A1 | 7/2010 | Andersen et al. |
| 2011/0154545 A1 | 6/2011 | Andersen et al. |
| 2013/0097730 A1* | 4/2013 | Narva ............... C12N 15/8286 800/279 |
| 2013/0097735 A1 | 4/2013 | Bowen et al. |
| 2013/0177539 A1* | 7/2013 | Broglie ................. A01N 63/00 424/93.21 |
| 2014/0194306 A1 | 7/2014 | Andersen et al. |
| 2014/0250552 A1 | 9/2014 | Broglie et al. |
| 2016/0230186 A1* | 8/2016 | Baum ............... C12N 15/8286 |

FOREIGN PATENT DOCUMENTS

| | | |
|---|---|---|
| WO | 2011/025860 A1 | 3/2011 |
| WO | 2013/192256 A1 | 12/2013 |
| WO | 2013192256 | 12/2013 |
| WO | 2014/153254 A2 | 9/2014 |
| WO | WO-2014153254 A2 * | 9/2014 ......... C12N 15/8218 |

OTHER PUBLICATIONS

Thomas et al. 2001, The Plant Journal 25(4):417-425.*
Yibrah et al. 1993, Hereditas 118:273-2890.*
International Search Report and Written Opinion for PCT/US2016/034515, dated Sep. 12, 2016, 12 pages.
NCBI, GenBank Accseesion No. XM_002424131.1, 'Prediculus humanus corporis transcription elongation factor SPT6, putative, mRNA', Aug. 3, 2009, 14 pages.
Bolognesi, et al., "Characterizing the mechanism of action of double-stranded RNA activity against western corn rootworm," PLOS ONE, Oct. 11, 2012, pp. 1-11, vol. 7, No. 10.
Rodrigues, et al., "Validation of reference housekeeping genes for gene expression studies in western corn rootworm," PLOS ONE, Oct. 30, 2014, p. e109825, vol. 9, No. 10.
Li, et al., "Long dsRNA but not siRNA initiates RNAi in western corn rootworm larvae and adults," Journal of Applied Entomology, Jul. 1, 2015, pp. 432-445, vol. 139, No. 6.
Extended European Search Report for European application No. 16804088.9, dated Sep. 20, 2018, 8 pages.
International Preliminary Report on Patentability for PCT/US2016/034515, dated Dec. 14, 2017, 8 pages.
International Search Report and Written Opinion for PCT/US2016/034515, dated Sep. 12, 2016.
NCBI, GenBank Accession No. XM_002424131.1, Prediculus humanus corporis transcription elongation factor SPT6, putative, mRNA, Aug. 3, 2009.

(Continued)

*Primary Examiner* — Li Zheng

(74) *Attorney, Agent, or Firm* — Magleby, Cataxinos & Greenwood, P.C.

(57) ABSTRACT

This disclosure concerns nucleic acid molecules and methods of use thereof for control of insect pests through RNA interference-mediated inhibition of target coding and transcribed non-coding sequences in insect pests, including coleopteran pests. The disclosure also concerns methods for making transgenic plants that express nucleic acid molecules useful for the control of insect pests, and the plant cells and plants obtained thereby.

31 Claims, 1 Drawing Sheet

Specification includes a Sequence Listing.

(56) References Cited

OTHER PUBLICATIONS

Baum et al., Control of coleopteran insect pests through RNA interference; Nature Biotechnology; vol. 25; No. 11; Nov. 2007 pp. 1322-1326.

* cited by examiner

FIG. 1. Generation of dsRNA from a single transcription template with a single pair of primers
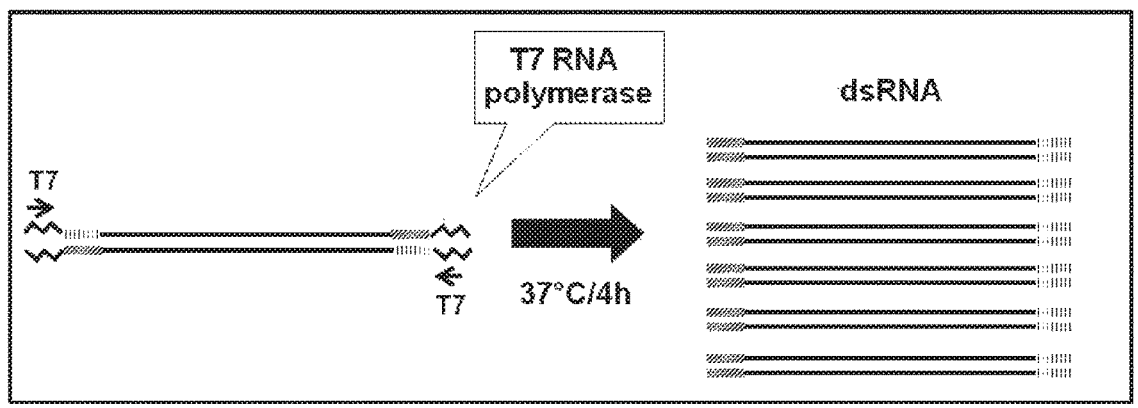
FIG. 2. Generation of dsRNA from two transcription templates.
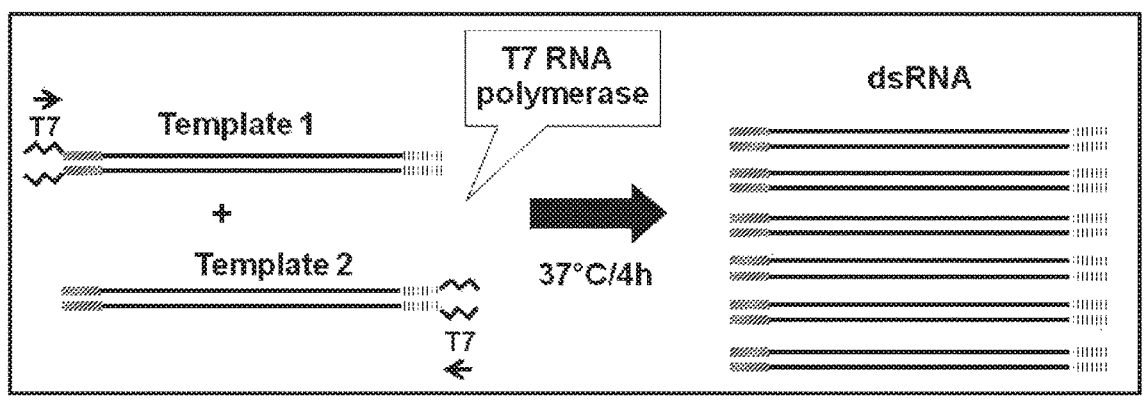

NUCLEIC ACID MOLECULES TO CONTROL INSECT PESTS

CROSS-REFERENCE TO RELATED APPLICATION

This application claims the benefit of the filing of U.S. Provisional Patent Application Ser. No. 62/168,606, filed May 29, 2015, the disclosure of which is hereby incorporated herein in its entirety by this reference.

TECHNICAL FIELD OF THE DISCLOSURE

The present invention relates generally to genetic control of plant damage caused by insect pests (e.g., coleopteran pests). In particular embodiments, the present invention relates to identification of target coding and non-coding polynucleotides, and the use of recombinant DNA technologies for post-transcriptionally repressing or inhibiting expression of target coding and non-coding polynucleotides in the cells of an insect pest to provide a plant protective effect.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in the Americas: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; *D. speciosa* Germar; and *D. u. undecimpunctata* Mannerheim. The United States Department of Agriculture has estimated that corn rootworms cause $1 billion in lost revenue each year, including $800 million in yield loss and $200 million in treatment costs.

Both WCR and NCR eggs are deposited in the soil during the summer. The insects remain in the egg stage throughout the winter. The eggs are oblong, white, and less than 0.004 inches in length. The larvae hatch in late May or early June, with the precise timing of egg hatching varying from year to year due to temperature differences and location. The newly hatched larvae are white worms that are less than 0.125 inches in length. Once hatched, the larvae begin to feed on corn roots. Corn rootworms go through three larval instars. After feeding for several weeks, the larvae molt into the pupal stage. They pupate in the soil, and then emerge from the soil as adults in July and August. Adult rootworms are about 0.25 inches in length.

Corn rootworm larvae complete development on corn and several other species of grasses. Larvae reared on yellow foxtail emerge later and have a smaller head capsule size as adults than larvae reared on corn. Ellsbury et al. (2005) Environ. Entomol. 34:627-34. WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis*), transgenic plants that express Bt toxins, or a combination thereof. Crop rotation suffers from the disadvantage of placing unwanted restrictions upon the use of farmland. Moreover, oviposition of some rootworm species may occur in soybean fields, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity to non-target species.

RNA interference (RNAi) is a process utilizing endogenous cellular pathways, whereby an interfering RNA (iRNA) molecule (e.g., a dsRNA molecule) that is specific for all, or any portion of adequate size, of a target gene results in the degradation of the mRNA encoded thereby. In recent years, RNAi has been used to perform gene "knockdown" in a number of species and experimental systems; for example, *Caenorhabditis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro ribonucleic acids (miRNAs) are structurally very similar molecules that are cleaved from precursor molecules containing a polynucleotide "loop" connecting the hybridized passenger and guide strands, and they may be similarly incorporated into RISC. Post-transcriptional gene silencing occurs when the guide strand binds specifically to a complementary mRNA molecule and induces cleavage by Argonaute, the catalytic component of the RISC complex. This process is known to spread systemically throughout the organism despite initially limited concentrations of siRNA and/or miRNA in some eukaryotes such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein. In insects, there are at least two DICER genes, where DICER1 facilitates miRNA-directed degradation by Argonaute1. Lee et al. (2004) Cell 117 (1):69-81. DICER2 facilitates siRNA-directed degradation by Argonaute2.

U.S. Pat. No. 7,612,194 and U.S. Patent Publication Nos. 2007/0050860, 2010/0192265, and 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. 2007/0050860 to operably link to a promoter a nucleic acid molecule that is complementary to one of several particular partial sequences of *D. v. virgifera* vacuolar-type ATPase (V-ATPase) disclosed therein for the expression of anti-sense RNA in plant cells. U.S. Patent Publication No. 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midguts, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. 2007/0050860, 2010/0192265, and 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. 2007/0050860, 2010/0192265, and 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA. U.S. Patent Application Publication No. U.S. 2013/040173 and PCT Application Publication No. WO 2013/169923 describe the use of a sequence derived from a *Diabrotica virgifera* Snf7 gene for RNA interference in maize. (Also disclosed in Bolognesi et al. (2012) PLoS ONE 7(10): e47534. doi:10.1371/journal.pone.0047534).

The overwhelming majority of sequences complementary to corn rootworm DNAs (such as the foregoing) do not provide a plant protective effect from species of corn rootworm when used as dsRNA or siRNA. For example, Baum et al. (2007) Nature Biotechnology 25:1322-1326, describe the effects of inhibiting several WCR gene targets by RNAi. These authors reported that 8 of the 26 target genes they tested were not able to provide experimentally significant coleopteran pest mortality at a very high iRNA (e.g., dsRNA) concentration of more than 520 ng/cm$^2$.

The authors of U.S. Pat. No. 7,612,194 and U.S. Patent Publication No. 2007/0050860 made the first report of in planta RNAi in corn plants targeting the western corn rootworm. Baum et al. (2007) Nat. Biotechnol. 25(11):1322-6. These authors describe a high-throughput in vivo dietary RNAi system to screen potential target genes for developing transgenic RNAi maize. Of an initial gene pool of 290 targets, only 14 exhibited larval control potential. One of the most effective double-stranded RNAs (dsRNA) targeted a gene encoding vacuolar ATPase subunit A (V-ATPase), resulting in a rapid suppression of corresponding endogenous mRNA and triggering a specific RNAi response with low concentrations of dsRNA. Thus, these authors documented for the first time the potential for in planta RNAi as a possible pest management tool, while simultaneously demonstrating that effective targets could not be accurately identified a priori, even from a relatively small set of candidate genes.

SUMMARY OF THE DISCLOSURE

Disclosed herein are nucleic acid molecules (e.g., target genes, DNAs, dsRNAs, siRNAs, miRNAs, shRNAs, and hpRNAs), and methods of use thereof, for the control of insect pests, including, for example, coleopteran pests, such as *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; *D. u. undecimpunctata* Mannerheim; and *D. speciosa* Germar. In particular examples, exemplary nucleic acid molecules are disclosed that may be homologous to at least a portion of one or more native nucleic acids in an insect pest.

In these and further examples, the native nucleic acid sequence may be a target gene, the product of which may be, for example and without limitation: involved in a metabolic process or involved in larval development. In some examples, post-transcriptional inhibition of the expression of a target gene by a nucleic acid molecule comprising a polynucleotide homologous thereto may be lethal to an insect pest or result in reduced growth and/or viability of an insect pest. In particular examples, a target gene useful for post-transcriptional inhibition is the gene referred to herein as SEQ ID NO:1. An isolated nucleic acid molecule comprising the polynucleotide of SEQ ID NO:1; the complement of SEQ ID NO:1; and/or fragments of either of the foregoing (e.g., SEQ ID NOs:2-3) is therefore disclosed herein.

Also disclosed are cDNA polynucleotides that may be used for the production of iRNA (e.g., dsRNA, siRNA, shRNA, miRNA, and hpRNA) molecules that are complementary to all or part of an insect pest target gene, for example, all or part of SEQ ID NO:1, SEQ ID NO:2, and/or SEQ ID NO:3. In particular embodiments, dsRNAs, siR- NAs, shRNAs, miRNAs, and/or hpRNAs may be produced in vitro or in vivo by a genetically-modified organism, such as a plant or bacterium. In particular examples, cDNA molecules are disclosed that may be used to produce iRNA molecules that are complementary to all or part of SEQ ID NO:1.

Disclosed are methods for controlling a population of an insect pest (e.g., a coleopteran pest), comprising providing to an insect pest (e.g., a coleopteran pest) an iRNA (e.g., dsRNA, siRNA, shRNA, miRNA, and hpRNA) molecule that functions upon being taken up by the pest to inhibit a biological function within the pest, wherein the iRNA molecule comprises all or part of a polynucleotide selected from the group consisting of: SEQ ID NO:79; the complement of SEQ ID NO:79; SEQ ID NO:80; the complement of SEQ ID NO:80; SEQ ID NO:81; the complement of SEQ ID NO:81; a polynucleotide that hybridizes to a native coding polynucleotide of a *Diabrotica* organism (e.g., WCR) comprising all or part of any of SEQ ID NOs:1-3; and the complement of a polynucleotide that hybridizes to a native coding polynucleotide of a *Diabrotica* organism comprising all or part of any of SEQ ID NOs:1-3.

In particular embodiments, an iRNA that functions upon being taken up by an insect pest to inhibit a biological function within the pest is transcribed from a DNA comprising all or part (e.g., 10 or more contiguous nucleotides) of a polynucleotide selected from the group consisting of: SEQ ID NO:1; the complement of SEQ ID NO:1; SEQ ID NO:2; the complement of SEQ ID NO:2; SEQ ID NO:3; the complement of SEQ ID NO:3; a native coding polynucleotide of a *Diabrotica* organism (e.g., WCR) comprising all or part of any of SEQ ID NOs:1-3; the complement of a native coding polynucleotide of a *Diabrotica* organism comprising all or part of any of SEQ ID NOs:1-3. Therefore, for example, an iRNA may be transcribed from a polynucleotide comprising at least 10 contiguous nucleotides of either of SEQ ID NO:2 or SEQ ID NO:3, such as a fragment of SEQ ID NO:1 that comprises at least 10 contiguous nucleotides of either of SEQ ID NO:2 or SEQ ID NO:3.

Also disclosed herein are methods wherein dsRNAs, siRNAs, shRNAs, miRNAs, and/or hpRNAs may be provided to an insect pest in a diet-based assay, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by the pest. Ingestion of dsRNAs, siRNA, shRNAs, miRNAs, and/or hpRNAs of the invention may then result in RNAi in the pest, which in turn may result in silencing of a gene essential for viability of the pest and leading ultimately to mortality. Thus, methods are disclosed wherein nucleic acid molecules comprising exemplary polynucleotide(s) useful for control of insect pests are provided to an insect pest. In particular examples, a coleopteran pest controlled by use of nucleic acid molecules of the invention may be WCR, NCR, SCR, *D. undecimpunctata howardi, D. balteata, D. undecimpunctata tenella, D. speciosa*, and *D. u. undecimpunctata*.

The foregoing and other features will become more apparent from the following Detailed Description of several embodiments, which proceeds with reference to the accompanying FIGS. 1-2.

BRIEF DESCRIPTION OF THE FIGURES

FIG. 1 includes a depiction of a strategy used to provide dsRNA from a single transcription template with a single pair of primers.

FIG. 2 includes a depiction of a strategy used to provide dsRNA from two transcription templates.

SEQUENCE LISTING

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NO:1 shows an exemplary WCR target gene DNA, referred to herein in some places as WCR tg-1 (target gene-1), which is used in some examples for the production of a dsRNA:

CGCCTTACACTCCAAGTGGTCAAACTCCATACATGACTCCGTACGCTACA

CCCCATACGCAGCAAACTCCCCGCTATGGTCATCAAACACCTTCCCAACA

CATGGCGAGCTCAGCACCACAAGGTCTCAACAATCCCTTTTTACATCCTG

GCGCGGTGACTCCCTCCCAACGAACTCCTATTTATCGCAACCATCCTGCA

CAATCTCCAGTAATGCTTCCTACAAGCCCTGTACCAAGTCCAGGTTCCCA

GAGTTCATACAGTAGTCATTTAAGTCATAATCAGCGAAGTGGAAGTTATG

CTGAATCCTTAAGATTCCAACCTCCCGAATCGCCGAGAAGCTCAGTGAGT

AATAGAAGCTTTCAAACTGATAGATACGGCGGTGATAGGTATGGTAAAGG

AGGAAGTCATAGATATGGTGGAAGCTCAAACGAAGATAGATATGGTAAGG

GAGGAGGAGGAAATGAAAATACGGATTGGCAGAAAGCTGCAGAAGCATG

SEQ ID NO:2 shows a further exemplary WCR target gene DNA, referred to herein in some places as WCR tg-1 v1 (version 1), which is used in some examples for the production of a dsRNA:

```
GACTCCGTACGCTACACCCCATACGCAGCAAACTCCCCGCTATGGICATC
AAACACCTTCCCAACACATGGCGAGCTCAGCACCACAAGGTCTCAACAAT
CCCTTTTTACATCCTGGCGCGGTGACTCCCTCCCAACGAACTCCT
```

SEQ ID NO:3 shows a further exemplary WCR target gene DNA, referred to herein in some places as WCR tg-1 v2 (version 2), which is used in some examples for the production of a dsRNA:

```
AGAGTTCATACAGTAGTCATTTAAGTCATAATCAGCGAAGTGGAAGTTATG
CTGAATCCTTAAGATTCCAACCTCCCGAATCGCCGAGAAGCTCAGTGAGTA
ATAGAA
```

SEQ ID NO:4 shows the nucleotide sequence of a T7 phage promoter.

SEQ ID NO:5 shows a fragment of an exemplary YFP coding region.

SEQ ID NOs:6-11 show primers used to amplify portions of exemplary WCR tg-1 polynucleotides comprising tg-1, tg-1 v1, and tg-1 v2, used in some examples for dsRNA production.

SEQ ID NO:12 shows an exemplary YFP gene.

SEQ ID NO:13 shows a DNA sequence of annexin region 1.

SEQ ID NO:14 shows a DNA sequence of annexin region 2.

SEQ ID NO:15 shows a DNA sequence of beta spectrin 2 region 1.

SEQ ID NO:16 shows a DNA sequence of beta spectrin 2 region 2.

SEQ ID NO:17 shows a DNA sequence of mtRP-L4 region 1.

SEQ ID NO:18 shows a DNA sequence of mtRP-L4 region 2.

SEQ ID NOs:19-46 show primers used to amplify gene regions of annexin, beta spectrin 2, mtRP-L4, and YFP for dsRNA synthesis.

SEQ ID NO:47 shows a maize DNA sequence encoding a TIP41-like protein.

SEQ ID NO:48 shows the nucleotide sequence of a T20VN primer oligonucleotide.

SEQ ID NOs:49-59 show primers and probes used for dsRNA transcript expression analyses in maize.

SEQ ID NO:60 shows a nucleotide sequence of a portion of a SpecR coding region used for binary vector backbone detection.

SEQ ID NO:61 shows a nucleotide sequence of an AAD1 coding region used for genomic copy number analysis.

SEQ ID NO:62 shows a DNA sequence of a maize invertase gene.

SEQ ID NOs:63-71 show the nucleotide sequences of DNA oligonucleotides used for gene copy number determinations and binary vector backbone detection.

SEQ ID NOs:72-77 show primers and probes that may be used for dsRNA transcript maize expression analyses in some embodiments.

SEQ ID NO:78 shows an exemplary linker polynucleotide, which forms a "loop" when transcribed in an RNA transcript to form a hairpin structure:

```
AGTCATCACGCTGGAGCGCACATATAGGCCCTCCATCAGAAAGTCATTGT
GTATATCTCTCATAGGGAACGAGCTGCTTGCGTATTTCCCTTCCGTAGTC
AGAGTCATCAATCAGCTGCACCGTGTCGTAAAGCGGGACGTTCGCAAGCT
CGT
```

SEQ ID NOs:79-81 show RNAs transcribed from nucleic acids comprising exemplary target gene (tg-1) polynucleotides and fragments thereof.

DETAILED DESCRIPTION

I. Overview of Several Embodiments

We developed RNA interference (RNAi) as a tool for insect pest management, using one of the most likely target pest species for transgenic plants that express dsRNA; the western corn rootworm. Thus far, most genes proposed as targets for RNAi in rootworm larvae do not actually achieve their purpose. Herein, we describe RNAi-mediated knock-down of a target gene in the exemplary insect pest, western corn rootworm, which is shown to have a lethal phenotype when, for example, iRNA are molecules delivered via ingested dsRNA directed against the target gene. In embodiments herein, the ability to deliver effective dsRNA by feeding to insects confers an RNAi effect that is very useful for insect (e.g., coleopteran) pest management. By combining the target gene herein with other useful RNAi targets, the potential to affect multiple target sequences, for example, in rootworms (e.g., larval rootworms), may increase opportunities to develop sustainable approaches to insect pest management involving RNAi technologies.

Disclosed herein are methods and compositions for genetic control of insect (e.g., coleopteran) pest infestations. Methods for identifying one or more gene(s) essential to the lifecycle of an insect pest for use as a target gene for RNAi-mediated control of an insect pest population are also provided. DNA plasmid vectors encoding an RNA molecule may be designed to suppress one or more target gene(s) essential for growth, survival, and/or development. In some embodiments, the RNA molecule may be capable of forming dsRNA molecules. In some embodiments, methods are provided for post-transcriptional repression of expression or inhibition of a target gene via nucleic acid molecules that are complementary to a coding or non-coding sequence of the target gene in an insect pest. In these and further embodiments, a pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, shRNA, miRNA, and/or hpRNA that is complementary to coding and/or non-coding sequences of the target gene(s) to achieve at least partial control of an insect (e.g., coleopteran) pest. Disclosed is a set of isolated and purified nucleic acid molecules comprising a polynucleotide, for example, as set forth in SEQ ID NO:1, fragments of SEQ ID NO:1, and the complements of the foregoing. In some embodiments, a stabilized dsRNA molecule may be expressed from these polynucleotides, fragments thereof, or a gene comprising one of these polynucleotides, for the post-transcriptional silencing or inhibition of a target gene. In certain embodiments, isolated and purified nucleic acid molecules comprise all or part of any of SEQ ID NOs:1-3, and/or the complement thereof.

Some embodiments involve a recombinant host cell (e.g., a plant cell) having in its genome at least one recombinant DNA encoding at least one iRNA (e.g., dsRNA) molecule(s). In particular embodiments, an encoded dsRNA molecule(s) may be provided when ingested by an insect (e.g., coleopteran) pest to post-transcriptionally silence or inhibit the expression of a target gene in the pest. The recombinant DNA may comprise, for example, any of SEQ ID NOs:1-3; fragments of any of SEQ ID NOs:1-3; and a polynucleotide consisting of a partial sequence of a gene comprising one of SEQ ID NOs:1-3; and/or complements thereof.

Some embodiments involve a recombinant host cell having in its genome a recombinant DNA encoding at least one iRNA (e.g., dsRNA) molecule(s) comprising all or part of SEQ ID NO:79 (e.g., at least one SEQ ID NO:80 and SEQ ID NO:81), of the complement thereof. When ingested by an insect (e.g., coleopteran) pest, the iRNA molecule(s) may silence or inhibit the expression of a target DNA (e.g., a DNA comprising all or part of a polynucleotide selected from the group consisting of SEQ ID NOs:1-3) in the pest or progeny of the pest, and thereby result in cessation of growth, development, viability, and/or feeding in the pest.

In some embodiments, a recombinant host cell having in its genome at least one recombinant DNA encoding at least one RNA molecule capable of forming a dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA(s). In particular embodiments, an RNA molecule capable of forming a dsRNA molecule may be expressed in a transgenic plant cell. Therefore, in these and other embodiments, a dsRNA molecule may be isolated from a transgenic plant cell. In particular embodiments, the transgenic plant is a plant selected from the group comprising corn (*Zea mays*) and plants of the family Poaceae.

Some embodiments involve a method for modulating the expression of a target gene in an insect (e.g., coleopteran) pest cell. In these and other embodiments, a nucleic acid molecule may be provided, wherein the nucleic acid molecule comprises a polynucleotide encoding an RNA molecule capable of forming a dsRNA molecule. In particular embodiments, a polynucleotide encoding an RNA molecule capable of forming a dsRNA molecule may be operatively linked to a promoter, and may also be operatively linked to a transcription termination sequence. In particular embodiments, a method for modulating the expression of a target gene in an insect pest cell may comprise: (a) transforming a plant cell with a vector comprising a polynucleotide encoding an RNA molecule capable of forming a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the RNA molecule capable of forming a dsRNA molecule encoded by the polynucleotide of the vector. A plant may be regenerated from a plant cell that has the vector integrated in its genome and comprises the dsRNA molecule encoded by the polynucleotide of the vector.

Thus, also disclosed is a transgenic plant comprising a vector having a polynucleotide encoding an RNA molecule capable of forming a dsRNA molecule integrated in its genome, wherein the transgenic plant comprises the dsRNA molecule encoded by the polynucleotide of the vector. In particular embodiments, expression of an RNA molecule capable of forming a dsRNA molecule in the plant is sufficient to modulate the expression of a target gene in a cell of an insect (e.g., coleopteran) pest that contacts the transformed plant or plant cell (for example, by feeding on the transformed plant, a part of the plant (e.g., root) or plant cell), such that growth and/or survival of the pest is inhibited. Transgenic plants disclosed herein may display protection and/or enhanced protection to insect pest infestations. Particular transgenic plants may display protection and/or enhanced protection to one or more coleopteran pest(s) selected from the group consisting of: WCR; NCR; SCR; MCR; *D. balteata* LeConte; *D. u. tenella; D. speciosa* Germar; and *D. u. undecimpunctata* Mannerheim.

Also disclosed herein are methods for delivery of control agents, such as an iRNA molecule, to an insect (e.g., coleopteran) pest. Such control agents may cause, directly or indirectly, an impairment in the ability of an insect pest population to feed, grow, or otherwise cause damage in a host. In some embodiments, a method is provided comprising delivery of a stabilized dsRNA molecule to an insect pest to suppress at least one target gene in the pest, thereby causing RNAi and reducing or eliminating plant damage in a host of the pest. In some embodiments, a method of inhibiting expression of a target gene in the insect pest may result in cessation of growth, survival, and/or development in the pest.

In some embodiments, compositions (e.g., a topical composition) are provided that comprise an iRNA (e.g., dsRNA) molecule for use in plants, animals, and/or the environment of a plant or animal to achieve the elimination or reduction of an insect (e.g., coleopteran) pest infestation. In particular embodiments, the composition may be a nutritional composition or food source to be fed to the insect pest. Some embodiments comprise making the nutritional composition or food source available to the pest. Ingestion of a composition comprising iRNA molecules may result in the uptake of the molecules by one or more cells of the pest, which may in turn result in the inhibition of expression of at least one target gene in cell(s) of the pest. Ingestion of or damage to a plant or plant cell by an insect pest infestation may be limited or eliminated in or on any host tissue or environment in which the pest is present by providing one or more compositions comprising an iRNA molecule in the host of the pest.

RNAi baits are formed when the dsRNA is mixed with food or an attractant or both. When the pests eat the bait, they also consume the dsRNA. Baits may take the form of granules, gels, flowable powders, liquids, or solids. In another embodiment, the dsRNA may be incorporated into a bait formulation such as that described in U.S. Pat. No. 8,530,440 which is hereby incorporated by reference. Generally, with baits, the baits are placed in or around the environment of the insect pest, for example, WCR can come into contact with, and/or be attracted to, the bait.

The compositions and methods disclosed herein may be used together in combinations with other methods and compositions for controlling damage by insect (e.g., coleopteran) pests. For example, an iRNA molecule as described herein for protecting plants from insect pests may be used in a method comprising the additional use of one or more chemical agents effective against an insect pest, biopesticides effective against such a pest, crop rotation, recombinant genetic techniques that exhibit features different from the features of RNAi-mediated methods and RNAi compositions (e.g., recombinant production of proteins in plants that are harmful to an insect pest (e.g., Bt toxins)), and/or recombinant expression of other iRNA molecules.

II. Abbreviations dsRNA double-stranded ribonucleic acid
GI growth inhibition
NCBI National Center for Biotechnology Information
gDNA genomic deoxyribonucleic acid
iRNA inhibitory ribonucleic acid
ORF open reading frame
RNAi ribonucleic acid interference
miRNA micro ribonucleic acid
shRNA small hairpin ribonucleic acid
siRNA small inhibitory ribonucleic acid
hpRNA hairpin ribonucleic acid
UTR untranslated region
WCR western corn rootworm (*Diabrotica virgifera virgifera* LeConte)
NCR northern corn rootworm (*Diabrotica barberi* Smith and Lawrence)
MCR Mexican corn rootworm (*Diabrotica virgifera zeae* Krysan and Smith)
PCR polymerase chain reaction
qPCR quantitative polymerase chain reaction
RISC RNA-induced Silencing Complex
SCR southern corn rootworm (*Diabrotica undecimpunctata howardi* Barber)
SEM standard error of the mean
YFP yellow fluorescent protein

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to pest insects of the order Coleoptera, including pest insects in the genus *Diabrotica*, which feed upon agricultural crops and crop products, including corn and other true grasses. In particular examples, a coleopteran pest is selected from a list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella*; *D. speciosa* Germar; and *D. u. undecimpunctata* Mannerheim.

Contact (with an organism): As used herein, the term "contact with" or "uptake by" an organism (e.g., a coleopteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize).

Expression: As used herein, "expression" of a coding polynucleotide (for example, a gene or a transgene) refers to the process by which the coded information of a nucleic acid transcriptional unit (including, e.g., gDNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Genetic material: As used herein, the term "genetic material" includes all genes, and nucleic acid molecules, such as DNA and RNA.

Inhibition: As used herein, the term "inhibition," when used to describe an effect on a coding polynucleotide (for example, a gene), refers to a measurable decrease in the cellular level of mRNA transcribed from the coding polynucleotide and/or peptide, polypeptide, or protein product of the coding polynucleotide. In some examples, expression of a coding polynucleotide may be inhibited such that expression is approximately eliminated. "Specific inhibition" refers to the inhibition of a target coding polynucleotide without consequently affecting expression of other coding polynucleotides (e.g., genes) in the cell wherein the specific inhibition is being accomplished.

Insect: As used herein with regard to pests, the term "insect pest" specifically includes coleopteran insect pests. In some examples, the term "insect pest" specifically refers to a coleopteran pest in the genus *Diabrotica* selected from a list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella*; *D. speciosa* Germar, and *D. u. undecimpunctata* Mannerheim.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, gDNA, and synthetic forms and mixed polymers of the above. A nucleotide or nucleobase may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement"

of a nucleic acid molecule refers to a polynucleotide having nucleobases that may form base pairs with the nucleobases of the nucleic acid molecule (i.e., A-T/U, and G-C).

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

```
ATGATGATG   polynucleotide

TACTACTAC   "complement" of the polynucleotide

CATCATCAT   "reverse complement" of the polynucleo-
            tide
```

Some embodiments of the invention may include hairpin RNA-forming RNAi molecules. In these RNAi molecules, both the complement of a nucleic acid to be targeted by RNA interference and the reverse complement may be found in the same molecule, such that the single-stranded RNA molecule may "fold over" and hybridize to itself over a region comprising the complementary and reverse complementary polynucleotides.

"Nucleic acid molecules" include all polynucleotides, for example: single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), shRNA (small hairpin RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, gDNA, and DNA-RNA hybrids. The terms "polynucleotide" and "nucleic acid," and "fragments" thereof will be understood by those in the art as a term that includes both gDNAs, ribosomal RNAs, transfer RNAs, messenger RNAs, operons, and smaller engineered polynucleotides that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleic acid, they may be used as probes for detecting DNA or RNA. Oligonucleotides composed of DNA (oligodeoxyribonucleotides) may be used in PCR, a technique for the amplification of DNAs. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding polynucleotide," "structural polynucleotide," or "structural nucleic acid molecule" refers to a polynucleotide that is ultimately translated into a polypeptide, via transcription and mRNA, when placed under the control of appropriate regulatory elements. With respect to RNA, the term "coding polynucleotide" refers to a polynucleotide that is translated into a peptide, polypeptide, or protein. The boundaries of a coding polynucleotide are determined by a translation start codon at the 5'-terminus and a translation stop codon at the 3'-terminus. Coding polynucleotides include, but are not limited to: gDNA; cDNA; EST; and recombinant polynucleotides.

As used herein, "transcribed non-coding polynucleotide" refers to segments of mRNA molecules such as 5'UTR, 3'UTR, and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18S rRNA, 23S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "spacer" in a nucleic acid and which is transcribed into an RNA molecule.

Lethal RNA interference: As used herein, the term "lethal RNA interference" refers to RNA interference that results in death or a reduction in viability of the subject individual to which, for example, a dsRNA, miRNA, siRNA, shRNA, and/or hpRNA is delivered.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell, such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome," as it applies to bacteria, refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two polynucleotides or polypeptides, refers to the residues in the sequences of the two molecules that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) of a molecule over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acids with even greater sequence similarity to the sequences of the reference polynucleotides will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleobases of the two nucleic acid molecules. The two molecules are then able to form hydrogen bonds with corresponding bases on the opposite strand to form a duplex molecule that, if it is sufficiently stable, is detectable using methods well known in the art. A polynucleotide need not be 100% complementary to its target nucleic acid to be specifically hybridizable. However, the amount of complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acids. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995.

As used herein, "stringent conditions" encompass conditions under which hybridization will only occur if there is less than 20% mismatch between the sequence of the hybridization molecule and a homologous polynucleotide within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects polynucleotides that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects polynucleotides that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (polynucleotides that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a nucleic acid, refers to a polynucleotide having contiguous nucleobases that hybridize under stringent conditions to the reference nucleic acid. For example, nucleic acids that are substantially homologous to a reference nucleic acid of any of SEQ ID NOs:1-3 are those nucleic acids that hybridize under stringent conditions (e.g., the Moderate Stringency conditions set forth, supra) to the reference nucleic acid. Substantially homologous polynucleotides may have at least 80% sequence identity. For example, substantially homologous polynucleotides may have from about 80% to 100% sequence identity, such as 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target polynucleotides under conditions where specific binding is desired, for example, under stringent hybridization conditions.

As used herein, the term "ortholog" refers to a gene in two or more species that has evolved from a common ancestral nucleic acid, and may retain the same function in the two or more species.

As used herein, two nucleic acid molecules are said to exhibit "complete complementarity" when every nucleotide of a polynucleotide read in the 5' to 3' direction is complementary to every nucleotide of the other polynucleotide when read in the 3' to 5' direction. A polynucleotide that is complementary to a reference polynucleotide will exhibit a sequence identical to the reverse complement of the reference polynucleotide. These terms and descriptions are well defined in the art and are easily understood by those of ordinary skill in the art.

Operably linked: A first polynucleotide is operably linked with a second polynucleotide when the first polynucleotide is in a functional relationship with the second polynucleotide. When recombinantly produced, operably linked polynucleotides are generally contiguous, and, where necessary to join two protein-coding regions, in the same reading frame (e.g., in a translationally fused ORF). However, nucleic acids need not be contiguous to be operably linked.

The term, "operably linked," when used in reference to a regulatory genetic element and a coding polynucleotide, means that the regulatory element affects the expression of the linked coding polynucleotide. "Regulatory elements," or "control elements," refer to polynucleotides that influence the timing and level/amount of transcription, RNA processing or stability, or translation of the associated coding polynucleotide. Regulatory elements may include promoters; translation leaders; introns; enhancers; stem-loop structures; repressor binding polynucleotides; polynucleotides with a termination sequence; polynucleotides with a polyadenylation recognition sequence; etc. Particular regulatory elements may be located upstream and/or downstream of a coding polynucleotide operably linked thereto. Also, particular regulatory elements operably linked to a coding polynucleotide may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding polynucleotide for expression in a cell, or a promoter may be operably linked to a polynucleotide encoding a signal peptide which may be operably linked to a coding polynucleotide for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; Int gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, XbA1/Nco1 fragment 5' to the *Brassica napus* ALS3 structural gene (or a polynucleotide similar to said XbA1/Nco1 fragment) (International PCT Publication No. WO96/30530).

Additionally, any tissue-specific or tissue-preferred promoter may be utilized in some embodiments of the invention. Plants transformed with a nucleic acid molecule comprising a coding polynucleotide operably linked to a tissue-specific promoter may produce the product of the coding polynucleotide exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); Agrobacterium-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid. In some examples, a transgene may be a DNA that encodes one or both strand(s) of an RNA capable of forming a dsRNA molecule that comprises a polynucleotide that is complementary to a nucleic acid molecule found in a coleopteran pest. In further examples, a transgene may be an antisense polynucleotide, wherein expression of the antisense polynucleotide inhibits expression of a target nucleic acid, thereby producing an RNAi phenotype. In still further examples, a transgene may be a gene (e.g., a herbicide-tolerance gene, a gene encoding an industrially or pharmaceutically useful compound, or a gene encoding a desirable agricultural trait). In these and other examples, a transgene may contain regulatory elements operably linked to a coding polynucleotide of the transgene (e.g., a promoter).

Vector: A nucleic acid molecule as introduced into a cell, for example, to produce a transformed cell. A vector may include genetic elements that permit it to replicate in the host cell, such as an origin of replication. Examples of vectors include, but are not limited to: a plasmid; cosmid; bacteriophage; or virus that carries exogenous DNA into a cell. A vector may also include one or more genes, including ones that produce antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% or greater relative to the yield of check varieties in the same growing location containing significant densities of the coleopteran pests that are injurious to that crop growing at the same time and under the same conditions, which are targeted by the compositions and methods herein.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising an Insect Pest Sequence

A. Overview

Described herein are nucleic acid molecules useful for the control of insect pests. In some examples, the insect pest is a coleopteran insect pest (e.g., a coleopteran pest in the genus *Diabrotica*). Described nucleic acid molecules include target polynucleotides (e.g., native genes, and non-coding polynucleotides), dsRNAs, siRNAs, shRNAs, hpRNAs, and miRNAs. For example, dsRNA, siRNA, miRNA, shRNA, and/or hpRNA molecules are described in some embodiments that may be specifically complementary to all or part of one or more native nucleic acids in a coleopteran pest. In these and further embodiments, the native nucleic acid(s) may be one or more target gene(s), the product of which may be, for example and without limitation: involved in a metabolic process or involved in larval development. Nucleic acid molecules described herein, when introduced into a cell comprising at least one native nucleic acid(s) to which the nucleic acid molecules are specifically complementary, may initiate RNAi in the cell, and consequently reduce or eliminate expression of the native nucleic acid(s). In some examples, reduction or elimination of the expression of a target gene by a nucleic acid molecule specifically complementary thereto may result in reduction or cessation of growth, development, viability, and/or feeding in the pest.

In some embodiments, at least one target gene in an insect pest may be selected, wherein the target gene comprises a polynucleotide selected from among SEQ ID NOs:1-3.

Provided according to the invention are DNAs, the expression of which results in an RNA molecule comprising a polynucleotide that is specifically complementary to all or part of a native RNA molecule that is encoded by a coding polynucleotide in an insect (e.g., coleopteran) pest. In some embodiments, after ingestion of the expressed RNA molecule by an insect pest, down-regulation of the coding polynucleotide in cells of the pest may be obtained. In particular embodiments, down-regulation of the coding polynucleotide in cells of the pest may be obtained. In particular embodiments, down-regulation of the coding polynucleotide in cells of the insect pest results in a deleterious effect on the growth and/or development of the pest.

In some embodiments, target polynucleotides include transcribed non-coding RNAs, such as 5'UTRs; 3'UTRs; spliced leaders; introns; outrons (e.g., 5'UTR RNA subsequently modified in trans splicing); donatrons (e.g., non-coding RNA required to provide donor sequences for trans splicing); and other non-coding transcribed RNA of target insect pest genes. Such polynucleotides may be derived from both mono-cistronic and poly-cistronic genes.

Thus, also described herein in connection with some embodiments are iRNA molecules (e.g., dsRNAs, siRNAs, miRNAs, shRNAs, and hpRNAs) that comprise at least one polynucleotide that is specifically complementary to all or part of a target nucleic acid in an insect (e.g., coleopteran) pest. In some embodiments an iRNA molecule may comprise polynucleotide(s) that are complementary to all or part of a plurality of target nucleic acids; for example, 2, 3, 4, 5, 6, 7, 8, 9, 10, or more target nucleic acids. In particular embodiments, an iRNA molecule may be produced in vitro, or in vivo by a genetically-modified organism, such as a plant or bacterium. Also disclosed are cDNAs that may be used for the production of dsRNA molecules, siRNA molecules, miRNA molecules, shRNA molecules, and/or hpRNA molecules that are specifically complementary to all or part of a target nucleic acid in an insect pest. Further described are recombinant DNA constructs for use in achieving stable transformation of particular host targets. Transformed host targets may express effective levels of dsRNA, siRNA, miRNA, shRNA, and/or hpRNA molecules from the recombinant DNA constructs. Therefore, also described is a plant transformation vector comprising at least one polynucleotide operably linked to a heterologous promoter functional in a plant cell, wherein expression of the polynucleotide(s) results in an RNA molecule comprising a string of contiguous nucleobases that is specifically complementary to all or part of a target nucleic acid in an insect pest.

In particular examples, nucleic acid molecules useful for the control of insect (e.g., coleopteran) pests may include: all or part of any of SEQ ID NOs:1-3; DNAs that when expressed result in an RNA molecule comprising a polynucleotide that is specifically complementary to all or part of a native RNA molecule that is encoded by all or part of SEQ ID NO:1, SEQ ID NO:2, or SEQ ID NO:3; iRNA molecules (e.g., dsRNAs, siRNAs, miRNAs, shRNAs, and hpRNAs) that comprise at least one polynucleotide that is specifically complementary to all or part of SEQ ID NO:1, SEQ ID NO:2, or SEQ ID NO:3; cDNAs that may be used for the production of dsRNA molecules, siRNA molecules, miRNA molecules, shRNA molecules, and/or hpRNA molecules that are specifically complementary to all or part of SEQ ID NO:1, SEQ ID NO:2, or SEQ ID NO:3; and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA, shRNA, and hpRNA) molecules that inhibit target gene expression in a cell, tissue, or organ of an insect (e.g., coleopteran) pest; and DNA molecules capable of being expressed as an iRNA molecule in a cell or microorganism to inhibit target gene expression in a cell, tissue, or organ of an insect pest.

Some embodiments of the invention provide an isolated nucleic acid molecule comprising at least one (e.g., one, two, three, or more) polynucleotide(s) selected from the group consisting of: SEQ ID NO:1; the complement of SEQ ID NO:1; a fragment of at least 15 contiguous nucleotides of SEQ ID NO:1 (e.g., either of SEQ ID NO:2 and SEQ ID NO:3); and the complement of a fragment of at least 15 contiguous nucleotides of SEQ ID NO:1.

In particular embodiments, contact with or uptake by an insect (e.g., coleopteran) pest of an iRNA transcribed from the isolated polynucleotide inhibits the growth, development, and/or feeding of the pest. In some embodiments, contact with or uptake by the insect occurs via feeding on plant material comprising the iRNA. In some embodiments, contact with or uptake by the insect occurs via spraying of a plant comprising the insect with a composition comprising the iRNA.

In some embodiments, an isolated nucleic acid molecule of the invention may comprise at least one (e.g., one, two, three, or more) polynucleotide(s) selected from the group consisting of: SEQ ID NO:79; the complement of SEQ ID NO:79; SEQ ID NO:80; the complement of SEQ ID NO:80; SEQ ID NO:81; the complement of SEQ ID NO:81; a fragment of at least 15 contiguous nucleotides of any of SEQ ID NOs:79-81; the complement of a fragment of at least 15 contiguous nucleotides of any of SEQ ID NOs:79-81; a fragment of at least 15 contiguous nucleotides of a native coding polynucleotide of a *Diabrotica* organism comprising any of SEQ ID NOs:1-3; and the complement of a fragment of at least 15 contiguous nucleotides of a native coding polynucleotide of a *Diabrotica* organism comprising any of SEQ ID NOs:1-3.

In particular embodiments, contact with or uptake by a coleopteran pest of the isolated polynucleotide inhibits the growth, development, and/or feeding of the pest.

In certain embodiments, dsRNA molecules provided by the invention comprise polynucleotides complementary to a transcript from a target gene comprising SEQ ID NO:1 or a fragment thereof, the inhibition of which target gene in an insect pest results in the reduction or removal of a polypeptide or polynucleotide agent that is essential for the pest's growth, development, or other biological function. A selected polynucleotide may exhibit from about 80% to about 100% sequence identity to any of SEQ ID NO:1; a contiguous fragment of SEQ ID NO:1; and the complement of either of the foregoing. For example, a selected polynucleotide may exhibit 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:1; a contiguous fragment of SEQ ID NO:1 (e.g., SEQ ID NO:2 or SEQ ID NO:3); or the complement of any of the foregoing.

In some embodiments, a DNA molecule capable of being expressed as an iRNA molecule in a cell or microorganism to inhibit target gene expression may comprise a single polynucleotide that is specifically complementary to all or part of a native polynucleotide found in one or more target insect pest species (e.g., a coleopteran pest species), or the DNA molecule can be constructed as a chimera from a plurality of such specifically complementary polynucleotides.

In some embodiments, a nucleic acid molecule may comprise a first and a second polynucleotide separated by a "spacer." A spacer may be a region comprising any sequence of nucleotides that facilitates secondary structure formation between the first and second polynucleotides, where this is desired. In one embodiment, the spacer is part of a sense or antisense coding polynucleotide for mRNA. The spacer may alternatively comprise any combination of nucleotides or homologues thereof that are capable of being linked covalently to a nucleic acid molecule. In some examples, the spacer may be a loop or intron (e.g., as ST-LS1 intron).

For example, in some embodiments, the DNA molecule may comprise a polynucleotide coding for one or more different iRNA molecules, wherein each of the different iRNA molecules comprises a first polynucleotide and a second polynucleotide, wherein the first and second polynucleotides are complementary to each other. The first and second polynucleotides may be connected within an RNA molecule by a spacer. The spacer may constitute part of the first polynucleotide or the second polynucleotide. Expression of an RNA molecule comprising the first and second nucleotide polynucleotides may lead to the formation of a dsRNA molecule, by specific intramolecular base-pairing of the first and second nucleotide polynucleotides. The first polynucleotide or the second polynucleotide may be substantially identical to a polynucleotide (e.g., a target gene, or transcribed non-coding polynucleotide) native to an insect pest (e.g., a coleopteran pest), a derivative thereof, or a complementary polynucleotide thereto.

dsRNA nucleic acid molecules comprise double strands of polymerized ribonucleotides, and may include modifications to either the phosphate-sugar backbone or the nucleoside.

Modifications in RNA structure may be tailored to allow specific inhibition. In one embodiment, dsRNA molecules may be modified through an ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNAs transcribed from a target gene, and both RNA molecules are subsequently degraded by an inherent cellular RNA-degrading mechanism. This process may result in the effective degradation or removal of the RNA encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in insect pests.

In some embodiments, a nucleic acid molecule may include at least one non-naturally occurring polynucleotide that can be transcribed into a single-stranded RNA molecule capable of forming a dsRNA molecule in vivo through intermolecular hybridization. Such dsRNAs typically self-assemble, and can be provided in the nutrition source of an insect (e.g., coleopteran) pest to achieve the post-transcriptional inhibition of a target gene. In these and further embodiments, a nucleic acid molecule may comprise two different non-naturally occurring polynucleotides, each of which is specifically complementary to a different target gene in an insect pest. When such a nucleic acid molecule is provided as a dsRNA molecule to, for example, a coleopteran pest, the dsRNA molecule inhibits the expression of at least two different target genes in the pest.

C. Obtaining Nucleic Acid Molecules

A variety of polynucleotides in insect (e.g., coleopteran) pests may be used as targets for the design of nucleic acid molecules, such as iRNAs and DNA molecules encoding iRNAs. Selection of native polynucleotides is not, however, a straight-forward process. For example, only a small number of native polynucleotides in a coleopteran pest will be effective targets. It cannot be predicted with certainty whether a particular native polynucleotide can be effectively down-regulated by nucleic acid molecules of the invention, or whether down-regulation of a particular native polynucleotide will have a detrimental effect on the growth, viability, and/or development of an insect pest. The vast majority of native coleopteran pest polynucleotides, such as ESTs isolated therefrom (for example, the coleopteran pest polynucleotides listed in U.S. Pat. No. 7,612,194), do not have a detrimental effect on the growth and/or viability of the pest. Neither is it predictable which of the native polynucleotides that may have a detrimental effect on an insect pest are able to be used in recombinant techniques for expressing nucleic acid molecules complementary to such native polynucleotides in a host plant and providing the detrimental effect on the pest upon feeding without causing harm to the host plant.

In some embodiments, nucleic acid molecules (e.g., dsRNA molecules to be provided in the host plant of an insect (e.g., coleopteran) pest) are selected to target cDNAs that encode proteins or parts of proteins essential for pest growth and/or development, such as polypeptides involved in metabolic or catabolic biochemical pathways, cell division, energy metabolism, digestion, host plant recognition, and the like. As described herein, ingestion of compositions by a target pest organism containing one or more dsRNAs, at least one segment of which is specifically complementary to at least a substantially identical segment of RNA produced in the cells of the target pest organism, can result in the death or other inhibition of the target. A polynucleotide, either DNA or RNA, derived from an insect pest can be used to construct plant cells protected against infestation by the pests. The host plant of the coleopteran pest (e.g., Z. mays), for example, can be transformed to contain one or more polynucleotides derived from the coleopteran pest as provided herein. The polynucleotide transformed into the host may encode one or more RNAs that form into a dsRNA structure in the cells or biological fluids within the transformed host, thus making the dsRNA available if/when the pest forms a nutritional relationship with the transgenic host. This may result in the suppression of expression of one or more genes in the cells of the pest, and ultimately death or inhibition of its growth or development.

Thus, in some embodiments, a gene is targeted that is essentially involved in the growth and development of an insect (e.g., coleopteran) pest. Other target genes for use in the present invention may include, for example, those that play important roles in pest viability, movement, migration, growth, development, infectivity, and establishment of feeding sites. A target gene may therefore be a housekeeping gene or a transcription factor. Additionally, a native insect pest polynucleotide for use in the present invention may also be derived from a homolog (e.g., an ortholog), of a plant, viral, bacterial or insect gene, the function of which is known to those of skill in the art, and the polynucleotide of which is specifically hybridizable with a target gene in the genome of the target pest. Methods of identifying a homolog of a gene with a known nucleotide sequence by hybridization are known to those of skill in the art.

In some embodiments, the invention provides methods for obtaining a nucleic acid molecule comprising a polynucleotide for producing an iRNA (e.g., dsRNA, siRNA, miRNA, shRNA, and hpRNA) molecule. One such embodiment comprises: (a) analyzing one or more target gene(s) for their expression, function, and phenotype upon dsRNA-mediated gene suppression in an insect (e.g., coleopteran) pest; (b) probing a cDNA or gDNA library with a probe comprising all or a portion of a polynucleotide or a homolog thereof from a targeted pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA or a homolog thereof; and (f) chemically synthesizing all or a substantial portion of a gene, or an siRNA, miRNA, hpRNA, mRNA, shRNA, or dsRNA.

In further embodiments, a method for obtaining a nucleic acid fragment comprising a polynucleotide for producing a substantial portion of an iRNA (e.g., dsRNA, siRNA, miRNA, shRNA, and hpRNA) molecule includes: (a) synthesizing first and second oligonucleotide primers specifically complementary to a portion of a native polynucleotide from a targeted insect (e.g., coleopteran) pest; and (b)

amplifying a cDNA or gDNA insert present in a cloning vector using the first and second oligonucleotide primers of step (a), wherein the amplified nucleic acid molecule comprises a substantial portion of a siRNA, miRNA, hpRNA, mRNA, shRNA, or dsRNA molecule.

Nucleic acids can be isolated, amplified, or produced by a number of approaches. For example, an iRNA (e.g., dsRNA, siRNA, miRNA, shRNA, and hpRNA) molecule may be obtained by PCR amplification of a target polynucleotide (e.g., a target gene or a target transcribed non-coding polynucleotide) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present invention may be produced chemically or enzymatically by one skilled in the art through manual or automated reactions, or in vivo in a cell comprising a nucleic acid molecule comprising a polynucleotide encoding the RNA, dsRNA, siRNA, miRNA, shRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of polynucleotides are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in an insect pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a polynucleotide that, upon expression to RNA and ingestion by an insect (e.g., coleopteran) pest, achieves suppression of a target gene in a cell, tissue, or organ of the pest. Thus, some embodiments provide a recombinant nucleic acid molecule comprising a polynucleotide capable of being expressed as an iRNA (e.g., dsRNA, siRNA, miRNA, shRNA, and hpRNA) molecule in a plant cell to inhibit target gene expression in an insect pest. In order to initiate or enhance expression, such recombinant nucleic acid molecules may comprise one or more regulatory elements, which regulatory elements may be operably linked to the polynucleotide capable of being expressed as an iRNA. Methods to express a gene suppression molecule in plants are known, and may be used to express a polynucleotide of the present invention. See, e.g., International PCT Publication No. WO06/073727; and U.S. Patent Publication No. 2006/0200878 A1)

In specific embodiments, a recombinant DNA molecule of the invention may comprise a polynucleotide encoding an RNA that may form a dsRNA molecule. Such recombinant DNA molecules may encode RNAs that may form dsRNA molecules capable of inhibiting the expression of endogenous target gene(s) in an insect (e.g., coleopteran) pest cell upon ingestion. In many embodiments, a transcribed RNA may form a dsRNA molecule that may be provided in a stabilized form; e.g., as a hairpin and stem and loop structure.

In some embodiments, one strand of a dsRNA molecule may be formed by transcription from a polynucleotide which is substantially homologous to a polynucleotide selected from the group consisting of SEQ ID NO:1; the complement of SEQ ID NO:1; a fragment of at least 15 contiguous nucleotides of SEQ ID NO:1, SEQ ID NO:2, or SEQ ID NO:3); and the complement of a fragment of at least 15 contiguous nucleotides of SEQ ID NO:1, SEQ ID NO:2, or SEQ ID NO:3.

In some embodiments, one strand of a dsRNA molecule may be formed by transcription from a polynucleotide that is substantially homologous to a polynucleotide selected from the group consisting of SEQ ID NOs:1-3; the complement of any of SEQ ID NOs:1-3; fragments of at least 15 contiguous nucleotides of SEQ ID NO:1; and the complements of fragments of at least 15 contiguous nucleotides of SEQ ID NO:1.

In particular embodiments, a recombinant DNA molecule encoding an RNA that may form a dsRNA molecule may comprise a coding region wherein at least two polynucleotides are arranged such that one polynucleotide is in a sense orientation, and the other polynucleotide is in an antisense orientation, relative to at least one promoter, wherein the sense polynucleotide and the antisense polynucleotide are linked or connected by a spacer of, for example, from about five (~5) to about one thousand (~1000) nucleotides. The spacer may form a loop between the sense and antisense polynucleotides. The sense polynucleotide or the antisense polynucleotide may be substantially homologous to a target gene (e.g., SEQ ID NO:1, SEQ ID NO:2, or SEQ ID NO:3) or fragment thereof. In some embodiments, however, a recombinant DNA molecule may encode an RNA that may form a dsRNA molecule without a spacer. In embodiments, a sense coding polynucleotide and an antisense coding polynucleotide may be different lengths.

Polynucleotides identified as having a deleterious effect on an insect pest or a plant-protective effect with regard to the pest may be readily incorporated into expressed dsRNA molecules through the creation of appropriate expression cassettes in a recombinant nucleic acid molecule of the invention. For example, such polynucleotides may be expressed as a hairpin with stem and loop structure by taking a first segment corresponding to a target gene polynucleotide (e.g., any of SEQ ID NOs:1-3, and fragments of any of the foregoing); linking this polynucleotide to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms comprising the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native insect (e.g., coleopteran) pest polynucleotide is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Certain embodiments of the invention include introduction of a recombinant nucleic acid molecule of the present invention into a plant (i.e., transformation) to achieve insect (e.g., coleopteran) pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acids of the invention can, for example, be suitably inserted into a vector under the control of a suitable promoter that functions in one or more hosts to drive expression of a linked coding polynucleotide or other DNA element. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart protection from an insect (e.g., coleopteran) pest to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a polynucleotide that is substantially homologous and specifically hybridizable to a corresponding transcribed polynucleotide within an insect pest that may cause damage to the host plant species. The pest may contact the iRNA molecule that is transcribed in cells of the transgenic host plant, for example, by ingesting cells or fluids of the transgenic host plant that comprise the iRNA molecule. Thus, in particular examples, expression of a target gene is suppressed by the iRNA molecule within coleopteran pests that infest the transgenic host plant. In some embodiments, suppression of expression of the target gene in a target coleopteran pest may result in the plant being protected against attack by the pest.

In order to enable delivery of iRNA molecules to an insect pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a polynucleotide of the invention operably linked to one or more regulatory elements, such as a heterologous promoter element that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); 5,641,876 (rice actin promoter); 6,426,446 (maize RS324 promoter); 6,429,362 (maize PR-1 promoter); 6,232,526 (maize A3 promoter); 6,177,611 (constitutive maize promoters); U.S. Pat. Nos. 5,322,938, 5,352,605, 5,359,142, and 5,530,196 (CaMV 35S promoter); 6,433,252 (maize L3 oleosin promoter); 6,429,357 (rice actin 2 promoter, and rice actin 2 intron); 6,294,714 (light-inducible promoters); 6,140,078 (salt-inducible promoters); 6,252,138 (pathogen-inducible promoters); 6,175,060 (phosphorous deficiency-inducible promoters); U.S. Pat. No. 6,388,170 (bidirectional promoters); 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a root-specific promoter. Root-specific promoters drive expression of operably-linked coding polynucleotides exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a polynucleotide or fragment for coleopteran pest control according to the invention may be cloned between two root-specific promoters oriented in opposite transcriptional directions relative to the polynucleotide or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by an insect pest so that suppression of target gene expression is achieved.

Additional regulatory elements that may optionally be operably linked to a nucleic acid include 5'UTRs located between a promoter element and a coding polynucleotide that function as a translation leader element. The translation leader element is present in fully-processed mRNA, and it may affect processing of the primary transcript, and/or RNA stability. Examples of translation leader elements include maize and *petunia* heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAntl; TEV (Carrington and Freed (1990) J. Virol. 64:1590-7); and AGRtunos (GenBank™ Accession No. V00087; and Bevan et al. (1983) Nature 304:184-7).

Additional regulatory elements that may optionally be operably linked to a nucleic acid also include 3' non-translated elements, 3' transcription termination regions, or polyadenylation regions. These are genetic elements located downstream of a polynucleotide, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation element can be derived from a variety of plant genes, or from T-DNA genes. A non-limiting example of a 3' transcription termination region is the nopaline synthase 3' region (nos 3; Fraley et al. (1983) Proc. Natl. Acad. Sci. USA 80:4803-7). An example of the use of different 3' non-translated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory elements operatively linked to one or more polynucleotides of the present invention. When expressed, the one or more polynucleotides result in one or more iRNA molecule(s) comprising a polynucleotide that is specifically complementary to all or part of a native RNA molecule in an insect (e.g., coleopteran) pest. Thus, the polynucleotide(s) may comprise a segment encoding all or part of a polyribonucleotide present within a targeted coleopteran pest RNA transcript, and may comprise inverted repeats of all or a part of a targeted pest transcript. A plant transformation vector may contain polynucleotides specifically complementary to more than one target polynucleotide, thus allowing production of more than one dsRNA for inhibiting expression of two or more genes in cells of one or more populations or species of target insect pests. Segments of polynucleotides specifically complementary to polynucleotides present in different genes can be combined into a single composite nucleic acid molecule for expression in a transgenic plant. Such segments may be contiguous or separated by a spacer.

In some embodiments, a plasmid of the present invention already containing at least one polynucleotide(s) of the invention can be modified by the sequential insertion of additional polynucleotide(s) in the same plasmid, wherein the additional polynucleotide(s) are operably linked to the same regulatory elements as the original at least one polynucleotide(s). In some embodiments, a nucleic acid molecule may be designed for the inhibition of multiple target genes. In some embodiments, the multiple genes to be inhibited can be obtained from the same insect (e.g., coleopteran) pest species, which may enhance the effectiveness of the nucleic acid molecule. In other embodiments, the genes can be derived from different insect pests, which may broaden the range of pests against which the agent(s) is/are effective. When multiple genes are targeted for suppression or a combination of expression and suppression, a polycistronic DNA element can be engineered.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide tolerance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate tolerance; a nitrilase gene which confers resistance to bromoxynil; a mutant acetolactate synthase (ALS) gene which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ *Stadler Genetics Symposium*, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to insect (e.g., coleopteran) pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by Agrobacterium-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acids encoding one or more iRNA molecules in the genome of the transgenic plant.

The most widely utilized method for introducing an expression vector into plants is based on the natural transformation system of Agrobacterium. A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border elements. The T-region may also contain a selectable marker for efficient recovery of transgenic cells and plants, and a multiple cloning site for inserting polynucleotides for transfer such as a dsRNA encoding nucleic acid.

Thus, in some embodiments, a plant transformation vector is derived from a Ti plasmid of A. tumefaciens (See, e.g., U.S. Pat. Nos. 4,536,475, 4,693,977, 4,886,937, and 5,501,967; and European Patent No. EP 0 122 791) or a Ri plasmid of A. rhizogenes. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as Sinorhizobium, Rhizobium, and Mesorhizobium that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA encoding one or more iRNA molecules that inhibit target gene expression in a coleopteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of gDNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to gDNA derived from any plant species (e.g., Z. mays) or tissue type, including cell cultures.

A transgenic plant formed using Agrobacterium-dependent transformation methods typically contains a single recombinant DNA inserted into one chromosome. The polynucleotide of the single recombinant DNA is referred to as a "transgenic event" or "integration event". Such transgenic plants are heterozygous for the inserted exogenous polynucleotide. In some embodiments, a transgenic plant homozygous with respect to a transgene may be obtained by sexually mating (selfing) an independent segregant transgenic plant that contains a single exogenous gene to itself, for example a To plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have an insect (e.g., coleopteran) pest-inhibitory effect. The iRNA molecules (e.g., dsRNA molecules) may be expressed from multiple nucleic acids introduced in different transformation events, or from a single nucleic acid introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple polynucleotides that are each homologous to different loci within one or more insect pests (for example, the locus defined by SEQ ID NO:1), both in different populations of the same species of insect pest, or in different species of insect pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a polynucleotide that encodes an iRNA molecule may be introduced into a first plant line that is amenable to transformation to produce a transgenic plant, which transgenic plant may be crossed with a second plant line to introgress the polynucleotide that encodes the iRNA molecule into the second plant line.

In some aspects, seeds and commodity products produced by transgenic plants derived from transformed plant cells are included, wherein the seeds or commodity products comprise a detectable amount of a nucleic acid of the invention. In some embodiments, such commodity products may be produced, for example, by obtaining transgenic plants and preparing food or feed from them. Commodity products comprising one or more of the polynucleotides of the invention includes, for example and without limitation: meals, oils, crushed or whole grains or seeds of a plant, and any food product comprising any meal, oil, or crushed or whole grain of a recombinant plant or seed comprising one or more of the nucleic acids of the invention. The detection of one or more of the polynucleotides of the invention in one or more commodity or commodity products is de facto evidence that the commodity or commodity product is produced from a transgenic plant designed to express one or more of the iRNA molecules of the invention for the purpose of controlling insect (e.g., coleopteran) pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran pest other than the one defined by SEQ ID NO:1, such as, for example, one or more loci selected from the group consisting of Caf1-180 (U.S. Patent Application Publication No. 2012/0174258), VatpaseC (U.S. Patent Application Publication No. 2012/0174259), Rho1 (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), ROP (U.S. patent application Ser. No. 14/577,811), RNA polymerase 11140 (U.S. patent application Ser. No. 14/577,854), Dre4 (U.S. patent application Ser. No. 14/705,807), ncm (U.S. Patent Application No. 62/095,487), COPI alpha (U.S. Patent Application No. 62/063,199), COPI beta (U.S. Patent Application No. 62/063,203), COPI gamma (U.S. Patent Application No. 62/063,192), COPI delta (U.S. Patent Application No. 62/063,216), RNA polymerase II (U.S. Patent Application No. 62/133,214), RNA polymerase 11-215 (U.S. Patent Application No. 62/133,202), RNA polymerase 33 (U.S. Patent Application No. 62/133,210), and histone chaperone spt5 (U.S. Patent Application No. 62/168,613); a transgenic event from which is transcribed an iRNA molecule targeting a gene in an organism other than a coleopteran pest (e.g., a plant-parasitic nematode); a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility. In particular embodiments, polynucleotides encoding iRNA molecules of the invention may be combined with other insect control and disease traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in an Insect Pest

A. Overview

In some embodiments of the invention, at least one nucleic acid molecule useful for the control of insect (e.g., coleopteran) pests may be provided to an insect pest, wherein the nucleic acid molecule leads to RNAi-mediated gene silencing in the pest. In particular embodiments, an iRNA molecule (e.g., dsRNA, siRNA, miRNA, shRNA, and hpRNA) may be provided to a coleopteran pest. In some embodiments, a nucleic acid molecule useful for the control of insect pests may be provided to a pest by contacting the nucleic acid molecule with the pest. In these and further embodiments, a nucleic acid molecule useful for the control of insect pests may be provided in a feeding substrate of the pest, for example, a nutritional composition. In these and further embodiments, a nucleic acid molecule useful for the control of an insect pest may be provided through ingestion of plant material comprising the nucleic acid molecule that is ingested by the pest. In certain embodiments, the nucleic acid molecule is present in plant material through expression of a recombinant nucleic acid introduced into the plant material, for example, by transformation of a plant cell with a vector comprising the recombinant nucleic acid and regeneration of a plant material or whole plant from the transformed plant cell.

B. RNAi-Mediated Target Gene Suppression

In some embodiments, the invention provides iRNA molecules (e.g., dsRNA, siRNA, miRNA, shRNA, and hpRNA) that may be designed to target essential native polynucleotides (e.g., essential genes) in the transcriptome of an insect pest (for example, a coleopteran (e.g., WCR, NCR, and SCR) pest), for example by designing an iRNA molecule that comprises at least one strand comprising a polynucleotide that is specifically complementary to the target polynucleotide. The sequence of an iRNA molecule so designed may be identical to that of the target polynucleotide, or may incorporate mismatches that do not prevent specific hybridization between the iRNA molecule and its target polynucleotide.

iRNA molecules of the invention may be used in methods for gene suppression in an insect (e.g., coleopteran) pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding polynucleotide including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In some embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand." The passenger strand may be degraded, and the guide strand may be incorporated into RISC. Post-transcriptional inhibition occurs by specific hybridization of the guide strand with a specifically complementary polynucleotide of an mRNA molecule, and subsequent cleavage by the enzyme, Argonaute (catalytic component of the RISC complex).

In some embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a polynucleotide, which polynucleotide may be expressed in vitro to produce an iRNA molecule that is substantially homologous to a nucleic acid molecule encoded by a polynucleotide within the genome of an insect (e.g., coleopteran) pest. In certain embodiments, the in vitro transcribed iRNA molecule may be a stabilized dsRNA molecule that comprises a stem-loop structure. After an insect pest contacts the in vitro transcribed iRNA molecule, post-transcriptional inhibition of a target gene in the pest (for example, an essential gene) may occur.

In some embodiments of the invention, expression of a nucleic acid molecule comprising at least 15 contiguous nucleotides (e.g., at least 19 contiguous nucleotides) of a polynucleotide are used in a method for post-transcriptional inhibition of a target gene in an insect (e.g., coleopteran) pest, wherein the polynucleotide is selected from the group consisting of: SEQ ID NO:1; the complement of SEQ ID NO:1; SEQ ID NO:2; the complement of SEQ ID NO:2; SEQ ID NO:3; the complement of SEQ ID NO:3; a fragment of at least 15 contiguous nucleotides of SEQ ID NO:1, SEQ ID NO:2, or SEQ ID NO:3; and the complement of a fragment of at least 15 contiguous nucleotides of SEQ ID NO:1, SEQ ID NO:2, or SEQ ID NO:3. In certain embodiments, expression of a nucleic acid molecule that is at least about 80% identical (e.g., 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of an insect (e.g., coleopteran) pest.

It is an important feature of some embodiments herein that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., polynucleotides substantially homologous to the iRNA molecule(s) are targeted for genetic inhibition. In some embodiments, an RNA molecule comprising a polynucleotide with a nucleotide sequence that is identical to that of a portion of a target gene may be used for inhibition. In these and further embodiments, an RNA molecule comprising a polynucleotide with one or more insertion, deletion, and/or point mutations relative to a target polynucleotide may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length polynucleotide exhibiting a greater homology compensates for a longer, less homologous polynucleotide. The length of the polynucleotide of a duplex region of a dsRNA molecule that is identical to a portion of a target gene transcript may be at least about 25, 50, 100, 200, 300, 400, 500, or at least about 1000 bases. In some embodiments, a polynucleotide of greater than 20-100 nucleotides may be used. In particular embodiments, a polynucleotide of greater than about 100-500 nucleotides may be used. In particular embodiments, a polynucleotide of greater than about 500-1000 nucleotides may be used, depending on the size of the target gene.

In certain embodiments, expression of a target gene in a pest (e.g., coleopteran) pest may be inhibited by at least 10%; at least 33%; at least 50%; or at least 80% within a cell of the pest, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although, in certain embodiments of the invention, inhibition occurs in substantially all cells of the pest, in other embodiments inhibition occurs only in a subset of cells expressing the target gene.

In some embodiments, transcriptional suppression is mediated by the presence in a cell of a dsRNA molecule exhibiting substantial sequence identity to a promoter DNA or the complement thereof to effect what is referred to as "promoter trans suppression." Gene suppression may be effective against target genes in an insect pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary polynucleotides in the cells of the insect pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of IRNA Molecules Provided to an Insect Pest

Expression of iRNA molecules for RNAi-mediated gene inhibition in an insect (e.g., coleopteran) pest may be carried out in any one of many in vitro or in vivo formats. The iRNA molecules may then be provided to an insect pest, for example, by contacting the iRNA molecules with the pest, or by causing the pest to ingest or otherwise internalize the iRNA molecules. Some embodiments include transformed host plants of a coleopteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by an insect pest during feeding, the pest may ingest iRNA molecules expressed in the transgenic plants or cells. The polynucleotides of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in an insect (e.g., coleopteran) pest comprises providing in the tissue of the host of the pest a gene-suppressive amount of at least one dsRNA molecule formed following transcription of a polynucleotide as described herein, at least one segment of which is complementary to an mRNA within the cells of the insect pest. A dsRNA molecule, including its modified form such as an siRNA, miRNA, shRNA, or hpRNA molecule, ingested by an insect pest may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from a polynucleotide selected from the group consisting of SEQ ID NOs:1-3. Isolated and substantially purified nucleic acid molecules including, but not limited to, non-naturally occurring polynucleotides and recombinant DNA constructs for providing dsRNA molecules are therefore provided, which suppress or inhibit the expression of an endogenous coding polynucleotide or a target coding polynucleotide in an insect pest when introduced thereto.

Particular embodiments provide a delivery system for the delivery of iRNA molecules for the post-transcriptional inhibition of one or more target gene(s) in an insect (e.g., coleopteran) plant pest and control of a population of the plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acids encoding a particular iRNA molecule may be produced by employing recombinant DNA technologies (which basic technologies are well-known in the art) to construct a plant transformation vector comprising a polynucleotide encoding an iRNA molecule of the invention (e.g., a stabilized dsRNA molecule); to transform a plant cell or plant; and to generate the transgenic plant cell or the transgenic plant that contains the transcribed iRNA molecule.

To impart insect (e.g., coleopteran) pest protection to a transgenic plant, a recombinant DNA molecule may, for example, be transcribed into an iRNA molecule, such as a dsRNA molecule, a siRNA molecule, a miRNA molecule, a shRNA molecule, or a hpRNA molecule. In some embodiments, an RNA molecule transcribed from a recombinant DNA molecule may form a dsRNA molecule within the tissues or fluids of the recombinant plant. Such a dsRNA molecule may be comprised in part of a polynucleotide that is identical to a corresponding polynucleotide transcribed from a DNA within an insect pest of a type that may infest the host plant. Expression of a target gene within the pest is suppressed by the dsRNA molecule, and the suppression of expression of the target gene in the pest results in the transgenic plant being protected against the pest. The modulatory effects of dsRNA molecules have been shown to be applicable to a variety of genes expressed in pests, including, for example, endogenous genes responsible for cellular metabolism or cellular transformation, including housekeeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a polynucleotide for use in producing iRNA molecules may be operably linked to one or more promoter elements functional in a plant host cell. The promoter may be an endogenous promoter, normally resident in the host genome. The polynucleotide of the present invention, under the control of an operably linked promoter element, may further be flanked by additional elements that advantageously affect its transcription and/or the stability of a resulting transcript. Such elements may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn plant) caused by an insect (e.g., coleopteran) pest that feeds on the plant, wherein the method comprises providing in the host plant a transformed plant cell expressing at least one nucleic acid molecule of the invention, wherein the nucleic acid molecule(s) functions upon being taken up by the pest(s) to inhibit the expression of a target polynucleotide within the pest(s), which inhibition of expression results in mortality and/or reduced growth of the pest(s), thereby reducing the damage to the host plant caused by the pest(s). In some embodiments, the nucleic acid molecule(s) comprise dsRNA molecules. In these and further embodiments, the nucleic acid molecule(s) comprise dsRNA molecules that each comprise more than one polynucleotide that is specifically hybridizable to a nucleic acid molecule expressed in a coleopteran pest cell. In some embodiments, the nucleic acid molecule(s) consist of one polynucleotide that is specifically hybridizable to a nucleic acid molecule expressed in an insect pest cell.

In some embodiments, a method for increasing the yield of a corn crop is provided, wherein the method comprises introducing into a corn plant at least one nucleic acid molecule of the invention; cultivating the corn plant to allow the expression of an iRNA molecule comprising the nucleic acid, wherein expression of an iRNA molecule comprising the nucleic acid inhibits insect (e.g., coleopteran) pest damage and/or growth, thereby reducing or eliminating a loss of yield due to pest infestation. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in an insect pest cell. In some examples, the nucleic acid molecule(s) comprises a polynucleotide that is specifically hybridizable to a nucleic acid molecule expressed in a coleopteran pest cell.

In some embodiments, a method for modulating the expression of a target gene in an insect (e.g., coleopteran) pest is provided, the method comprising: transforming a plant cell with a vector comprising a polynucleotide encoding at least one iRNA molecule of the invention, wherein the polynucleotide is operatively-linked to a promoter and a transcription termination element; culturing the transformed plant cell under conditions sufficient to allow for development of a plant cell culture including a plurality of transformed plant cells; selecting for transformed plant cells that have integrated the polynucleotide into their genomes; screening the transformed plant cells for expression of an iRNA molecule encoded by the integrated polynucleotide; selecting a transgenic plant cell that expresses the iRNA molecule; and feeding the selected transgenic plant cell to the insect pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in an insect pest cell. In some examples, the nucleic acid molecule(s) comprises a polynucleotide that is specifically hybridizable to a nucleic acid molecule expressed in a coleopteran pest cell.

iRNA molecules of the invention can be incorporated within the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to insect (e.g., coleopteran) pests. For example, the iRNA molecules of the invention may be directly introduced into the cells of a pest(s). Methods for introduction may include direct mixing of iRNA with plant tissue from a host for the insect pest(s), as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the insect pests known to infest the plant. iRNA molecules produced by chemical or enzymatic synthesis may also be formulated in a manner consistent with common agricultural practices, and used as spray-on or bait products for controlling plant damage by an insect pest. The formulations may include the appropriate stickers and wetters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from the pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1: Materials and Methods

Sample Preparation and Bioassays

A number of dsRNA molecules (including those corresponding to tg-1 (SEQ ID NO:1), tg-1 v1 (SEQ ID NO:2), and tg-1 v2 (SEQ ID NO:3) were synthesized and purified using a MEGASCRIPT® RNAi kit or HiScribe® T7 In Vitro Transcription Kit. The purified dsRNA molecules were prepared in TE buffer, and all bioassays contained a control treatment consisting of this buffer, which served as a background check for mortality or growth inhibition of WCR (*Diabrotica virgifera virgifera* LeConte). The concentrations of dsRNA molecules in the bioassay buffer were measured using a NANODROP™ 8000 spectrophotometer (THERMO SCIENTIFIC, Wilmington, Del.).

Samples were tested for insect activity in bioassays conducted with neonate insect larvae on artificial insect diet. WCR eggs were obtained from CROP CHARACTERISTICS, INC. (Farmington, Minn.).

The bioassays were conducted in 128-well plastic trays specifically designed for insect bioassays (C-D INTERNA- TIONAL, Pitman, N.J.). Each well contained approximately 1.0 mL of an artificial diet designed for growth of coleopteran insects. A 60 µL aliquot of dsRNA sample was delivered by pipette onto the surface of the diet of each well (40 µL/cm$^2$). dsRNA sample concentrations were calculated as the amount of dsRNA per square centimeter (ng/cm$^2$) of surface area (1.5 cm$^2$) in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light:Dark)) for 9 days, after which time the total number of insects exposed to each sample, the number of dead insects, and the weight of surviving insects were recorded. Average percent mortality and average growth inhibition were calculated for each treatment. Growth inhibition (GI) was calculated as follows:

$$GI=[1-(TWIT/TNIT)/(TWIBC/TNIBC)],$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

The statistical analysis was done using JMP™ software (SAS, Cary, N.C.).

The LC$_{50}$ (Lethal Concentration) is defined as the dosage at which 50% of the test insects are killed. The GI$_{50}$ (Growth Inhibition) is defined as the dosage at which the mean growth (e.g. live weight) of the test insects is 50% of the mean value seen in Background Check samples.

Replicated bioassays demonstrated that ingestion of particular samples resulted in a surprising and unexpected mortality and growth inhibition of corn rootworm larvae.

Example 2: Identification of Candidate Target Genes

Insects from multiple stages of WCR (*Diabrotica virgifera virgifera* LeConte) development were selected for pooled transcriptome analysis to provide candidate target gene sequences for control by RNAi transgenic plant insect protection technology.

In one exemplification, total RNA was isolated from about 0.9 gm whole first-instar WCR larvae; (4 to 5 days post-hatch; held at 16° C.), and purified using the following phenol/TRI REAGENT®-based method (MOLECULAR RESEARCH CENTER, Cincinnati, Ohio):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 µL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 gm of larvae yielded over 1 mg of total RNA, with an A$_{260}$/A$_{280}$ ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA; 1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1×TAE was used as the running buffer. Before use, the electrophoresis tank and the well-forming comb were cleaned with RNaseAway™ (INVITROGEN INC., Carlsbad, Calif.). Two µL of RNA sample were mixed with 8 µL of TE buffer (10 mM Tris HCl pH 7.0; 1 mM EDTA) and 10 µL of RNA sample buffer (NOVAGEN® Catalog No 70606; EMD4 Bioscience, Gibbstown, N.J.). The sample was heated at 70° C. for 3 min, cooled to room temperature, and 5 µL (containing 1 µg to 2 µg RNA) were loaded per well. Commercially available RNA molecular weight markers were simultaneously run in separate wells for molecular size comparison. The gel was run at 60 volts for 2 hrs.

A normalized cDNA library was prepared from the larval total RNA by a commercial service provider (EUROFINS MWG Operon, Huntsville, Ala.), using random priming. The normalized larval cDNA library was sequenced at ½ plate scale by GS FLX 454 Titanium™ series chemistry at EUROFINS MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for RNAi targeting were those hypothesized to be essential for survival and growth in coleopteran insects. Selected target gene homologs were identified in the transcriptome sequence database as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than e' for contig homologies and better than e$^{-10}$ for unassembled sequence read homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit to the non-*Diabrotica* candidate gene sequence present in the *Diabrotica* sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, Sequencher™ v4.9 (GENE CODES CORPORATION, Ann Arbor, Mich.) was used to assemble the sequences into longer contigs.

A candidate *Diabrotica* target gene (SEQ ID NO:1) was identified as a gene that may lead to coleopteran pest mortality, inhibition of growth, or inhibition of development in WCR.

SEQ ID NO:1 is novel. The sequence is not provided in public databases, and is not disclosed in PCT International Patent Publication No. WO/2011/025860; U.S. Patent Application No. 20070124836; U.S. Patent Application No. 20090306189; U.S. Patent Application No. US20070050860; U.S. Patent Application No. 20100192265; U.S. Pat. No. 7,612,194; or U.S. Patent Application No. 2013192256.

dsRNA transgenes targeting SEQ ID NO:1, SEQ ID NO:2, or SEQ ID NO:3 can be combined with other dsRNA molecules to provide redundant RNAi targeting and synergistic RNAi effects. Transgenic corn events expressing dsRNA that targets tg-1 are useful for preventing root feeding damage by corn rootworm. Furthermore, these dsRNA transgenes represent new modes of action for combining with *Bacillus thuringiensis* insecticidal protein technology in Insect Resistance Management gene pyramids to mitigate against the development of rootworm populations resistant to either of these rootworm control technologies.

Full-length or partial clones of sequences of the *Diabrotica* candidate gene, herein referred to as target gene-1 (SEQ ID NO:1), were used to generate PCR amplicons for dsRNA synthesis.

Example 3: Amplification of Target Genes to Produce dsRNA

Full-length or partial clones of sequences of the *Diabrotica* candidate gene were used to generate PCR amplicons for dsRNA synthesis. Primers were designed to amplify portions of coding regions of each target gene by PCR. See Table 1. Where appropriate, a T7 phage promoter sequence (TTAATACGACTCACTATAGGGAGA; SEQ ID NO:4) was incorporated into the 5' ends of the amplified sense or antisense strands. See Table 1. Total RNA was extracted from WCR using TRIzol® (Life Technologies, Grand Island, N.Y.), and was then used to make first-strand cDNA with SuperScriptIII® First-Strand Synthesis System and manufacturers Oligo dT primed instructions (Life Technologies, Grand Island, N.Y.). First-strand cDNA was used as template for PCR reactions using opposing primers positioned to amplify all or part of the native target gene sequence. dsRNA was also amplified from a DNA clone comprising the coding region for a yellow fluorescent protein (YFP) (SEQ ID NO:5; Shagin et al. (2004) Mol. Biol. Evol. 21(5):841-50).

Table 1. Primers and Primer Pairs used to amplify portions of coding regions of exemplary target gene-1 and YFP negative control gene.

|        | Gene ID     | Primer ID          | Sequence                                                              |
|--------|-------------|--------------------|-----------------------------------------------------------------------|
| Pair 1 | spt6-1      | Dvv-spt6-1_For     | TTAATACGACTCACTATAGGGAGACGCCT TACACTCCAAGTGGTCAAAC (SEQ ID NO: 6)     |
|        |             | Dvv-spt6-1_Rev     | TTAATACGACTCACTATAGGGAGACATGC TTCTGCAGCTTTCTGCCAATC (SEQ ID NO: 7)    |
| Pair 2 | spt6-1 v1   | Dvv-spt6-1_v1_For  | TTAATACGACTCACTATAGGGAGAGACTC CGTACGCTACACCCCATAC (SEQ ID NO: 8)      |
|        |             | Dvv-spt6-1_v1_Rev  | TTAATACGACTCACTATAGG GAGAAGGAG TTCGTTGGGAGGGAGTCAC (SEQ ID NO: 9)     |
| Pair 3 | spt6-1 v2   | Dvv-spt6-1_v2_For  | TTAATACGACTCACTATAGGGAGAAGAGT TCATACAGTAGTCATTTAAGTC (SEQ ID NO: 10)  |
|        |             | Dvv-spt6-1_v2_Rev  | TTAATACGACTCACTATAGGGAGATTCTA TTACTCACTGAGCTTCTCG (SEQ ID NO: 11)     |
| Pair 4 | YFP         | YFP-F T7           | TTAATACGACTCACTATAGGGAGACACCA TGGGCTCCAGCGGCGCCC (SEQ ID NO: 19)      |
|        |             | YFP-R T7           | TTAATACGACTCACTATAGGGAGAAGATC TTGAAGGCGCTCTTCAGG (SEQ ID NO: 22)      |

Example 4: RNAi Constructs

Template Preparation by PCR and dsRNA Synthesis

A strategy used to provide specific templates for target gene and YFP dsRNA production is shown in FIG. 1. Template DNAs intended for use in target gene dsRNA synthesis were prepared by PCR using the primer pairs in Table 1 and (as PCR template) first-strand cDNA prepared from total RNA isolated from WCR eggs, first-instar larvae, or adults. For each selected target gene and YFP target gene region, PCR amplifications introduced a T7 promoter sequence at the 5' ends of the amplified sense and antisense strands (the YFP segment was amplified from a DNA clone of the YFP coding region). The two PCR amplified fragments for each region of the target genes were then mixed in approximately equal amounts, and the mixture was used as transcription template for dsRNA production. See FIG. 1. The sequences of the dsRNA templates amplified with the particular primer pairs were: SEQ ID NO:1 (target gene-1), SEQ ID NO:2 (tg-1 v1), SEQ ID NO:3 (tg-1 v2), and SEQ ID NO:5 (YFP). Double-stranded RNA for insect bioassay was synthesized and purified using an AMBION® MIEGASCRIPT® RNAi kit following the manufacturer's instructions (INVITROGEN) or HiScribe® T7 In Vitro Transcription Kit following the manufacturer's instructions (New England Biolabs, Ipswich, Mass.). The concentrations of dsRNAs were measured using a NANODROP™ 8000 spectrophotometer (THERMO SCIENTIFIC, Wilmington, Del.).

Construction of Plant Transformation Vectors

Entry vectors harboring a target gene construct for hairpin formation comprising segments of target gene-1 (SEQ ID NO:1) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of the target gene segment in opposite orientation to one another, the two segments being separated by a linker polynucleotide (e.g., a loop (such as SEQ ID NO:78) and an ST-LS1 intron (Vancanneyt et al. (1990) Mol. Gen. Genet. 220(2):245-50)). Thus, the primary mRNA transcript contains the two target gene segment sequences as large inverted repeats of one another, separated by the linker sequence. A copy of a promoter (e.g., maize ubiquitin 1, U.S. Pat. No. 5,510,474; 35S from Cauliflower Mosaic Virus (CaMV); Sugarcane bacilliform badnavirus (ScBV) promoter; promoters from rice actin genes; ubiquitin promoters; pEMU; MAS; maize H3 histone promoter; ALS promoter; phaseolin gene promoter; cab; rubisco; LAT52; Zm13; and/or apg) is used to drive production of the primary mRNA hairpin transcript, and a fragment comprising a 3' untranslated region (e.g., a maize peroxidase 5 gene (ZmPer5 3'UTR v2; U.S. Pat. No. 6,699,984), AtUbi10, AtEf1, or StPinII) is used to terminate transcription of the hairpin-RNA-expressing gene.

Entry vectors are used in standard GATEWAY® recombination reactions with a typical binary destination vector to produce hairpin RNA expression transformation vectors for *Agrobacterium*-mediated maize embryo transformations.

The binary destination vector comprises a herbicide tolerance gene (aryloxyalknoate dioxygenase; AAD-1 v3) (U.S. Pat. No. 7,838,733(B2), and Wright et al. (2010) Proc. Natl. Acad. Sci. U.S.A. 107:20240-5) under the regulation of a plant operable promoter (e.g., sugarcane bacilliform badnavirus (ScBV) promoter (Schenk et al. (1999) Plant Mol. Biol. 39:1221-30) or ZmUbi1 (U.S. Pat. No. 5,510,474)). A 5'UTR and linker are positioned between the 3' end of the promoter segment and the start codon of the AAD-1 coding region. A fragment comprising a 3' untranslated region from a maize lipase gene (ZmLip 3'UTR; U.S. Pat. No. 7,179,902) is used to terminate transcription of the AAD-1 mRNA.

A negative control binary vector, which comprises a gene that expresses a YFP protein, is constructed by means of standard GATEWAY® recombination reactions with a typical binary destination vector and entry vector. The binary destination vector comprises a herbicide tolerance gene (aryloxyalknoate dioxygenase; AAD-1 v3) (as above) under the expression regulation of a maize ubiquitin 1 promoter (as above) and a fragment comprising a 3' untranslated region from a maize lipase gene (ZmLip 3'UTR; as above). The entry vector comprises a YFP coding region (SEQ ID NO:12) under the expression control of a maize ubiquitin 1 promoter (as above) and a fragment comprising a 3' untranslated region from a maize peroxidase 5 gene (as above).

Example 5: Screening of Candidate Target Genes

Synthetic dsRNA designed to inhibit target gene sequences identified in EXAMPLE 2 caused mortality and growth inhibition when administered to WCR in diet-based assays.

Replicated bioassays demonstrated that ingestion of dsRNA preparations derived from tg-1, tg-1 v1, and tg-1 v2 resulted in mortality and growth inhibition of western corn rootworm larvae. Table 2 shows the results of diet-based feeding bioassays of WCR larvae following 9-day exposure to tg-1, tg-1 v1, and tg-1 v2 dsRNA, as well as the results obtained with a negative control sample of dsRNA prepared from a yellow fluorescent protein (YFP) coding region (SEQ ID NO:5). Table 3 shows the $LC_{50}$ and $GI_{50}$ results of exposure to tg-1 v1 and tg-1 v2 dsRNA.

TABLE 2

Results of feeding assays obtained with western corn rootworm larvae after 9 days of feeding on diet containing target gene-1, tg-1 v1, and tg-1 v2 dsRNA. ANOVA analysis found significance differences in Mean % Mortality and Mean % Growth Inhibition (GI). Means were separated using the Tukey-Kramer test.

| Gene Name | Dose (ng/cm$^2$) | N | Mean (% Mortality) ± SEM* | Mean (GI) ± SEM |
|---|---|---|---|---|
| target gene-1 | 500 | 4 | 89.51 ± 4.35 (A) | 0.98 ± 0.00 (A) |
| tg-1 v1 | 500 | 9 | 85.06 ± 4.17 (A) | 0.98 ± 0.01 (A) |
| tg-1 v2 | 500 | 9 | 85.49 ± 2.91 (A) | 0.98 ± 0.01 (A) |
| TE** | 0 | 20 | 6.93 ± 1.86 (B) | 0.01 ± 0.05 (BC) |
| WATER | 0 | 16 | 7.32 ± 1.98 (B) | −0.09 ± 0.03 (C) |
| YFP*** | 500 | 16 | 11.91 ± 3.54 (B) | 0.09 ± 0.07 (B) |

*SEM = Standard Error of the Mean. Letters in parentheses designate statistical levels. Levels not connected by same letter are significantly different (P < 0.05).
**TE = Tris HCl (1 mM) plus EDTA (0.1 mM) buffer, pH 7.2.
***YFP = Yellow Fluorescent Protein

TABLE 3

Summary of oral potency of tg-1 v1 and tg-1 v2 dsRNA on WCR larvae (ng/cm$^2$).

| Gene Name | $LC_{50}$ | Range | $GI_{50}$ | Range |
|---|---|---|---|---|
| tg-1 v1 | 46.41 | 34.40-63.29 | 18.22 | 11.28-29.43 |
| tg-1 v2 | 13.05 | 8.88-18.88 | 2.92 | 1.60-5.33 |

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,612,194, which discloses 9,112 sequences. However, it was determined that many genes suggested to have utility for RNAi-mediated insect control are not efficacious in controlling *Diabrotica*. It was also determined that sequence tg-1, tg-1 v1, and tg-1 v2 dsRNA provide surprising and unexpected superior control of *Diabrotica*, compared to other genes suggested to have utility for RNAi-mediated insect control.

For example, annexin, beta spectrin 2, and mtRP-L4 were each suggested in U.S. Pat. No. 7,612,194 to be efficacious in RNAi-mediated insect control. SEQ ID NO:13 is the DNA sequence of annexin region 1 (Reg 1) and SEQ ID NO:14 is the DNA sequence of annexin region 2 (Reg 2). SEQ ID NO:15 is the DNA sequence of beta spectrin 2 region 1 (Reg 1) and SEQ ID NO:16 is the DNA sequence of beta spectrin 2 region 2 (Reg2). SEQ ID NO:17 is the DNA sequence of mtRP-L4 region 1 (Reg 1) and SEQ ID NO:18 is the DNA sequence of mtRP-L4 region 2 (Reg 2). A YFP sequence (SEQ ID NO:5) was also used to produce dsRNA as a negative control.

Each of the aforementioned sequences was used to produce dsRNA by the methods of EXAMPLE 3. The strategy used to provide specific templates for dsRNA production is shown in FIG. 2. Template DNAs intended for use in dsRNA synthesis were prepared by PCR using the primer pairs in Table 4 and (as PCR template) first-strand cDNA prepared from total RNA isolated from WCR first-instar larvae. (YFP was amplified from a DNA clone.) For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. See FIG. 2. Double-stranded RNA was synthesized and purified using an AMBION® MiEGAscript® RNAi kit following the manufacturer's instructions (INVITROGEN). The concentrations of dsRNAs were measured using a NANODROP™ 8000 spectrophotometer (THERMO SCIENTIFIC, Wilmington, Del.) and the dsRNAs were each tested by the same diet-based bioassay methods described above. Table 4 lists the sequences of the primers used to produce the annexin Reg1, annexin Reg2, beta spectrin 2 Reg1, beta spectrin 2 Reg2, mtRP-L4 Reg1, mtRP-L4 Reg2, and YFP dsRNA molecules. Table 5 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, water, or YFP protein.

TABLE 4

Primers and Primer Pairs used to amplify portions of coding regions of genes.

| | Gene (Region) | Primer ID | Sequence |
|---|---|---|---|
| Pair 5 | YFP | YFP-F_T7 | TTAATACGACTCACTATAGGGAGACACCATG GGCTCCAGCGGCGCCC (SEQ ID NO: 19) |
| | YFP | YFP-R | AGATCTTGAAGGCGCTCTTCAGG (SEQ ID NO: 20) |
| Pair 6 | YFP | YFP-F | CACCATGGGCTCCAGCGGCGCCC (SEQ ID NO: 21) |
| | YFP | YFP-R_T7 | TTAATACGACTCACTATAGGGAGAAGATCTT GAAGGCGCTCTTCAGG (SEQ ID NO: 22) |
| Pair 7 | Annexin (Reg 1) | Ann-F1_T7 | TTAATACGACTCACTATAGGGAGAGCTCCAA CAGTGGTTCCTTATC (SEQ ID NO: 23) |
| | Annexin (Reg 1) | Ann-R1 | CTAATAATTCTTTTTTAATGTTCCTGAGG (SEQ ID NO: 24) |
| Pair 8 | Annexin (Reg 1) | Ann-F1 | GCTCCAACAGTGGTTCCTTATC (SEQ ID NO: 25) |
| | Annexin (Reg 1) | Ann-R1_T7 | TTAATACGACTCACTATAGGGAGACTAATAA TTCTTTTTTAATGTTCCTGAGG (SEQ ID NO:26) |
| Pair 9 | Annexin (Reg 2) | Ann-F2_T7 | TTAATACGACTCACTATAGGGAGATTGTTAC AAGCTGGAGAACTTCTC (SEQ ID NO: 29) |
| | Annexin (Reg 2) | Ann-R2 | CTTAACCAACAACGGCTAATAAGG (SEQ ID NO: 28) |
| Pair 10 | Annexin (Reg 2) | Ann-F2 | TTGTTACAAGCTGGAGAACTTCTC (SEQ ID NO: 29) |
| | Annexin (Reg 2) | Ann-R2_T7 | TTAATACGACTCACTATAGGGAGACTTAACC AACAACGGCTAATAAGG (SEQ ID NO: 30) |
| Pair 11 | Beta-spect2 (Reg 1) | Betasp2-F1_T7 | TTAATACGACTCACTATAGGGAGAAGATGTT GGCTGCATCTAGAGAA (SEQ ID NO: 31) |
| | Beta-spect2 (Reg 1) | Betasp2-R1 | GTCCATTCGTCCATCCACTGCA (SEQ ID NO: 32) |
| Pair 12 | Beta-spect2 (Reg 1) | Betasp2-F1 | AGATGTTGGCTGCATCTAGAGAA (SEQ ID NO: 33) |
| | Beta-spect2 (Reg 1) | Betasp2-R1_T7 | TTAATACGACTCACTATAGGGAGAGTCCATT CGTCCATCCACTGCA (SEQ ID NO: 34) |
| Pair 13 | Beta-spect2 (Reg 2) | Betasp2-F2_T7 | TTAATACGACTCACTATAGGGAGAGCAGATG AACACCAGCGAGAAA (SEQ ID NO: 35) |
| | Beta-spect2 (Reg 2) | Betasp2-R2 | CTGGGCAGCTTCTTGTTTCCTC (SEQ ID NO: 36) |
| Pair 14 | Beta-spect2 (Reg 2) | Betasp2-F2 | GCAGATGAACACCAGCGAGAAA (SEQ ID NO: 37) |
| | Beta-spect2 (Reg 2) | Betasp2-R2_T7 | TTAATACGACTCACTATAGGGAGACTGGGCA GCTTCTTGTTTCCTC (SEQ ID NO: 38) |
| Pair 15 | mtRP-L4 (Reg 1) | L4-F1_T7 | TTAATACGACTCACTATAGGGAGAAGTGAAA TGTTAGCAAATATAACATCC (SEQ ID NO: 39) |

TABLE 4-continued

Primers and Primer Pairs used to amplify portions of coding regions of genes.

| | Gene (Region) | Primer ID | Sequence |
|---|---|---|---|
| | mtRP-L4 (Reg 1) | L4-R1 | ACCTCTCACTTCAAATCTTGACTTTG (SEQ ID NO: 40) |
| Pair 16 | mtRP-L4 (Reg 1) | L4-F1 | AGTGAAATGTTAGCAAATATAACATCC (SEQ ID NO: 41) |
| | mtRP-L4 (Reg 1) | L4-R1_T7 | TTAATACGACTCACTATAGGGAGAACCTCTC ACTTCAAATCTTGACTTTG (SEQ ID NO: 42) |
| Pair 17 | mtRP-L4 (Reg 2) | L4-F2_T7 | TTAATACGACTCACTATAGGGAGACAAAGTC AAGATTTGAAGTGAGAGGT (SEQ ID NO: 43) |
| | mtRP-L4 (Reg 2) | L4-R2 | CTACAAATAAAACAAGAAGGACCCC (SEQ ID NO: 44) |
| Pair 18 | mtRP-L4 (Reg 2) | L4-F2 | CAAAGTCAAGATTTGAAGTGAGAGGT (SEQ ID NO: 45) |
| | mtRP-L4 (Reg 2) | L4-R2_T7 | TTAATACGACTCACTATAGGGAGACTACAAA TAAAACAAGAAGGACCCC (SEQ ID NO: 46) |

TABLE 5

Results of diet feeding assays obtained with western corn rootworm larvae after 9 days.

| Gene Name | Dose (ng/cm$^2$) | Mean Live Larval Weight (mg) | Mean % Mortality | Mean Growth Inhibition |
|---|---|---|---|---|
| annexin-Reg 1 | 1000 | 0.545 | 0 | −0.262 |
| annexin-Reg 2 | 1000 | 0.565 | 0 | −0.301 |
| beta spectrin2 Reg 1 | 1000 | 0.340 | 12 | −0.014 |
| beta spectrin2 Reg 2 | 1000 | 0.465 | 18 | −0.367 |
| mtRP-L4 Reg 1 | 1000 | 0.305 | 4 | −0.168 |
| mtRP-L4 Reg 2 | 1000 | 0.305 | 7 | −0.180 |
| TE buffer* | 0 | 0.430 | 13 | 0.000 |
| Water | 0 | 0.535 | 12 | 0.000 |
| YFP** | 1000 | 0.480 | 9 | −0.386 |

*TE = Tris HCl (10 mM) plus EDTA (1 mM) buffer, pH 8.
**YFP = Yellow Fluorescent Protein Example 6: Production of Transgenic Maize Tissues Comprising Insecticidal dsRNAs

*Agrobacterium*-Mediated Transformation.

Transgenic maize cells, tissues, and plants that produce one or more insecticidal dsRNA molecules (for example, at least one dsRNA molecule including a polyribonucleotide targeting SEQ ID NO:1 (e.g., SEQ ID NOs:2-3)) through expression of a chimeric gene stably-integrated into the plant genome are produced following *Agrobacterium*-mediated transformation. Maize transformation methods employing superbinary or binary transformation vectors are known in the art, as described, for example, in U.S. Pat. No. 8,304,604, which is herein incorporated by reference in its entirety. Transformed tissues are selected by their ability to grow on Haloxyfop-containing medium and are screened for dsRNA production, as appropriate. Portions of such transformed tissue cultures may be presented to neonate corn rootworm larvae for bioassay, essentially as described in EXAMPLE 1.

*Agrobacterium* Culture Initiation.

Glycerol stocks of *Agrobacterium* strain DAt13192 cells (PCT International Publication No. WO 2012/016222A2) harboring a binary transformation vector described above (EXAMPLE 4) are streaked on AB minimal medium plates (Watson, et al. (1975) J. Bacteriol. 123:255-264) containing appropriate antibiotics, and are grown at 20° C. for 3 days. The cultures are then streaked onto YEP plates (gm/L: yeast extract, 10; Peptone, 10; NaCl, 5) containing the same antibiotics and are incubated at 20° C. for 1 day.

*Agrobacterium* Culture.

On the day of an experiment, a stock solution of Inoculation Medium and acetosyringone is prepared in a volume appropriate to the number of constructs in the experiment and pipetted into a sterile, disposable, 250 mL flask. Inoculation Medium (Frame et al. (2011) *Genetic Transformation Using Maize Immature Zygotic Embryos*. IN Plant Embryo Culture Methods and Protocols: Methods in Molecular Biology. T. A. Thorpe and E. C. Yeung, (Eds), Springer Science and Business Media, LLC. pp 327-341) contains: 2.2 gm/L MS salts; 1×ISU Modified MS Vitamins (Frame et al., ibid.) 68.4 gm/L sucrose; 36 gm/L glucose; 115 mg/L L-proline; and 100 mg/L myo-inositol; at pH 5.4.) Acetosyringone is added to the flask containing Inoculation Medium to a final concentration of 200 µM from a 1 M stock solution in 100% dimethyl sulfoxide, and the solution is thoroughly mixed.

For each construct, 1 or 2 inoculating loops-full of *Agrobacterium* from the YEP plate are suspended in 15 mL Inoculation Medium/acetosyringone stock solution in a sterile, disposable, 50 mL centrifuge tube, and the optical density of the solution at 550 nm ($OD_{550}$) is measured in a spectrophotometer. The suspension is then diluted to $OD_{550}$ of 0.3 to 0.4 using additional Inoculation Medium/acetosyringone mixtures. The tube of *Agrobacterium* suspension is then placed horizontally on a platform shaker set at about 75 rpm at room temperature and shaken for 1 to 4 hours while embryo dissection is performed.

Ear Sterilization and Embryo Isolation.

Maize immature embryos are obtained from plants of *Zea mays* inbred line B104 (Hanauer et al. (1997) Crop Science 37:1405-1406), grown in the greenhouse and self- or sib-pollinated to produce ears. The ears are harvested approximately 10 to 12 days post-pollination. On the experimental day, de-husked ears are surface-sterilized by immersion in a 20% solution of commercial bleach (ULTRA CLOROX® Germicidal Bleach, 6.15% sodium hypochlorite; with two drops of TWEEN 20) and shaken for 20 to 30 min, followed by three rinses in sterile deionized water in a laminar flow hood. Immature zygotic embryos (1.8 to 2.2 mm long) are aseptically dissected from each ear and randomly distributed into microcentrifuge tubes containing 2.0 mL of a suspension of appropriate *Agrobacterium* cells in liquid Inoculation Medium with 200 µM acetosyringone, into which 2 µL of 10% BREAK-THRU® 5233 surfactant (EVONIK INDUSTRIES; Essen, Germany) is added. For a given set of experiments, embryos from pooled ears are used for each transformation.

*Agrobacterium* Co-Cultivation.

Following isolation, the embryos are placed on a rocker platform for 5 minutes. The contents of the tube are then poured onto a plate of Co-cultivation Medium, which contains 4.33 gm/L MS salts; 1×ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L AgNO$_3$; 200 µM acetosyringone in DMSO; and 3 gm/L GELZAN™, at pH 5.8. The liquid *Agrobacterium* suspension is removed with a sterile, disposable, transfer pipette. The embryos are then oriented with the scutellum facing up using sterile forceps with the aid of a microscope. The plate is closed, sealed with 3M™ MICROPORE™ medical tape, and placed in an incubator at 25° C. with continuous light at approximately 60 µmol m$^{-2}$ s$^{-1}$ of Photosynthetically Active Radiation (PAR).

Callus Selection and Regeneration of Transgenic Events.

Following the Co-Cultivation period, embryos are transferred to Resting Medium, which is composed of 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L AgNO$_3$; 0.5 gm/L MES (2-(N-morpholino)ethanesulfonic acid monohydrate; PHYTOTECHNOLOGIES LABR; Lenexa, Kans.); 250 mg/L Carbenicillin; and 2.3 gm/L GELZAN™; at pH 5.8. No more than 36 embryos are moved to each plate. The plates are placed in a clear plastic box and incubated at 27° C. with continuous light at approximately 50 µmol m$^{-2}$ s$^{-1}$ PAR for 7 to 10 days. Callused embryos are then transferred (<18/plate) onto Selection Medium I, which is comprised of Resting Medium (above) with 100 nM R-Haloxyfop acid (0.0362 mg/L; for selection of calli harboring the AAD-1 gene). The plates are returned to clear boxes and incubated at 27° C. with continuous light at approximately 50 µmol m$^{-2}$ s$^{-1}$ PAR for 7 days. Callused embryos are then transferred (<12/plate) to Selection Medium II, which is comprised of Resting Medium (above) with 500 nM R-Haloxyfop acid (0.181 mg/L). The plates are returned to clear boxes and incubated at 27° C. with continuous light at approximately 50 µmol m$^{-2}$ s$^{-1}$ PAR for 14 days. This selection step allows transgenic callus to further proliferate and differentiate.

Proliferating, embryogenic calli are transferred (<9/plate) to Pre-Regeneration medium. Pre-Regeneration Medium contains 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L AgNO$_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 0.181 mg/L Haloxyfop acid; at pH 5.8. The plates are stored in clear boxes and incubated at 27° C. with continuous light at approximately 50 µmol m$^{-2}$ s$^{-1}$ PAR for 7 days. Regenerating calli are then transferred (<6/plate) to Regeneration Medium in PHYTATRAYS™ (SIGMA-ALDRICH) and incubated at 28° C. with 16 hours light/8 hours dark per day (at approximately 160 µmol m$^{-2}$ s$^{-1}$ PAR) for 14 days or until shoots and roots develop. Regeneration Medium contains 4.33 gm/L MS salts; 1×ISU Modified MS Vitamins; 60 gm/L sucrose; 100 mg/L myo-inositol; 125 mg/L Carbenicillin; 3 gm/L GELLAN™ gum; and 0.181 mg/L R-Haloxyfop acid; at pH 5.8. Small shoots with primary roots are then isolated and transferred to Elongation Medium without selection. Elongation Medium contains 4.33 gm/L MS salts; 1×ISU Modified MS Vitamins; 30 gm/L sucrose; and 3.5 gm/L GELRITE™: at pH 5.8.

Transformed plant shoots selected by their ability to grow on medium containing Haloxyfop are transplanted from PHYTATRAYS™ to small pots filled with growing medium (PROMIX BX; PREMIER TECH HORTICULTURE), covered with cups or HUMI-DOMES (ARCO PLASTICS), and then hardened-off in a CONVIRON growth chamber (27° C. day/24° C. night, 16-hour photoperiod, 50-70% RH, 200 µmol m$^{-2}$ s$^{-1}$ PAR). In some instances, putative transgenic plantlets are analyzed for transgene relative copy number by quantitative real-time PCR assays using primers designed to detect the AAD1 herbicide tolerance gene integrated into the maize genome. Further, qPCR assays are used to detect the presence of the linker sequence and/or of target sequence in putative transformants. Selected transformed plantlets are then moved into a greenhouse for further growth and testing.

Transfer and Establishment of to Plants in the Greenhouse for Bioassay and Seed Production.

When plants reach the V3-V4 stage, they are transplanted into IE CUSTOM BLEND (PROFILE/METRO MIX 160) soil mixture and grown to flowering in the greenhouse (Light Exposure Type: Photo or Assimilation; High Light Limit: 1200 PAR; 16-hour day length; 27° C. day/24° C. night).

Plants to be used for insect bioassays are transplanted from small pots to TINUS™ 350-4 ROOTRAINERS® (SPENCER-LEMAIRE INDUSTRIES, Acheson, Alberta, Canada;) (one plant per event per ROOTRAINER®). Approximately four days after transplanting to ROOTRAINERS®, plants are infested for bioassay.

Plants of the T$_1$ generation are obtained by pollinating the silks of T$_0$ transgenic plants with pollen collected from plants of non-transgenic inbred line B104 or other appropriate pollen donors, and planting the resultant seeds. Reciprocal crosses are performed when possible.

Example 7: Molecular Analyses of Transgenic Maize Tissues

Molecular analyses (e.g. RT-qPCR) of maize tissues are performed on samples from leaves and/or roots that were collected from greenhouse grown plants on the day before or same days that root feeding damage is assessed.

Results of RT-qPCR assays for the target gene are used to validate expression of the transgenes. Results of RT-qPCR assays for intervening sequence between repeat sequences (which is integral to the formation of dsRNA hairpin molecules) in expressed RNAs can also be used to validate the presence of hairpin transcripts. Transgene RNA expression levels are measured relative to the RNA levels of an endogenous maize gene.

DNA qPCR analyses to detect a portion of the AAD1 coding region in gDNA are used to estimate transgene insertion copy number. Samples for these analyses are collected from plants grown in environmental chambers. Results are compared to DNA qPCR results of assays designed to detect a portion of a single-copy native gene, and simple events (having one or two copies of iRNA transgenes) are advanced for further studies in the greenhouse.

Additionally, qPCR assays designed to detect a portion of the spectinomycin-resistance gene (SpecR; harbored on the binary vector plasmids outside of the T-DNA) are used to determine if the transgenic plants contain extraneous integrated plasmid backbone sequences.

RNA Transcript Expression Level:

Target qPCR. Callus cell events or transgenic plants are analyzed by real time quantitative PCR (qPCR) of the target sequence to determine the relative expression level of the transgene, as compared to the transcript level of an internal maize gene (for example, GENBANK Accession No. BT069734), which encodes a TIP41-like protein (i.e. a maize homolog of GENBANK Accession No. AT4G34270; having a tBLASTX score of 74% identity). RNA is isolated using Norgen BioTek™ Total RNA Isolation Kit (Norgen, Thorold, ON). The total RNA is subjected to an On Column DNase1 treatment according to the kit's suggested protocol. The RNA is then quantified on a NANODROP 8000 spectrophotometer (THERMO SCIENTIFIC) and the concentration is normalized to 50 ng/μL. First strand cDNA is prepared using a HIGH CAPACITY cDNA SYNTHESIS KIT (INVITROGEN) in a 10 μL reaction volume with 5 denatured RNA, substantially according to the manufacturer's recommended protocol. The protocol is modified slightly to include the addition of 10 μL of 100 μM T20VN oligonucleotide (IDT) (TTTTTTTTTTTTTTTTTTTTVN, where V is A, C, or G, and N is A, C, G, or T; SEQ ID NO:48) into the 1 mL tube of random primer stock mix, in order to prepare a working stock of combined random primers and oligo dT.

Following cDNA synthesis, samples are diluted 1:3 with nuclease-free water, and stored at −20° C. until assayed. Separate real-time PCR assays for the target gene and TIP41-like transcript are performed on a LIGHTCYCLER™ 480 (ROCHE DIAGNOSTICS, Indianapolis, Ind.) in 10 reaction volumes. For the target gene assay, reactions are run with Primers tg1v1_62 F (SEQ ID NO:56) and tg1v1_360 R (SEQ ID NO:54), and an IDT Custom Oligo probe tg1 PRB Set1, labeled with FAM and double quenched with Zen and Iowa Black quenchers. For the TIP41-like reference gene assay, primers TIPmxF (SEQ ID NO:51) and TIPmxR (SEQ ID NO:52), and Probe HXTIP (SEQ ID NO:53) labeled with HEX (hexachlorofluorescein) are used.

All assays include negative controls of no-template (mix only). For the standard curves, a blank (water in source well) is also included in the source plate to check for sample cross-contamination. Primer and probe sequences are set forth in Table 6. Reaction components recipes for detection of the various transcripts are disclosed in Table 7, and PCR reactions conditions are summarized in Table 8. The FAM (6-Carboxy Fluorescein Amidite) fluorescent moiety is excited at 465 nm and fluorescence is measured at 510 nm; the corresponding values for the HEX (hexachlorofluorescein) fluorescent moiety are 533 nm and 580 nm.

TABLE 6

Oligonucleotide sequences used for molecular analyses of transcript levels in transgenic maize.

| Target | Oligonucleotide | Sequence |
| --- | --- | --- |
| tg-1v1 | tg1v1_62 F | AAGATCCTGCCTGAACCTGC (SEQ ID NO: 56) |
| tg-1v1 | tg1v1_360 R | GGAAATACGCAAGCAGCTCG (SEQ ID NO: 54) |
| tg-1v1 | tg1v1_224 P | CATCCTGGCGCGGTGACTCC (SEQ ID NO: 55) |
| tg-1v2 | tg1v2_86 F | TCCTGCAAGAACGTGGGTAC (SEQ ID NO: 59) |
| tg-1v2 | tg1v2_323 R | GGAAATACGCAAGCAGCTCG (SEQ ID NO: 57) |
| tg-1v2 | tg1v2_182 P | CCAACCTCCCGAATCGCCGA (SEQ ID NO: 58) |
| TIP41 | TIPmxF | TGAGGGTAATGCCAACTGGTT (SEQ ID NO: 51) |
| TIP41 | TIPmxR | GCAATGTAACCGAGTGTCTCTCAA (SEQ ID NO: 52) |
| TIP41 | HXTIP (HEX-Probe) | TTTTTGGCTTAGAGTTGATGGTGTACTGATGA (SEQ ID NO: 53) |

*TIP41-like protein.

TABLE 7

PCR reaction recipes for transcript detection.

| Component | Target Gene | TIP-like Gene |
| --- | --- | --- |
| | Final Concentration | |
| Roche Buffer | 1 X | 1X |
| tg-1 FWD Set 1 | 0.4 μM | 0 |
| tg-1 REV Set 1 | 0.4 μM | 0 |
| tg-1 FAM | 0.2 μM | 0 |
| HEXtipZM F | 0 | 0.4 μM |
| HEXtipZM R | 0 | 0.4 μM |
| HEXtipZMP (HEX) | 0 | 0.2 μM |
| cDNA (2.0 μL) | NA | NA |
| Water | To 10 μL | To 10 μL |

TABLE 8

Thermocycler conditions for RNA qPCR.
Target Gene and TIP41-like Gene Detection

| Process | Temp. | Time | No. Cycles |
| --- | --- | --- | --- |
| Target Activation | 95° C. | 10 min | 1 |
| Denature | 95° C. | 10 sec | 40 |
| Extend | 60° C. | 40 sec | |

TABLE 8-continued

Thermocycler conditions for RNA qPCR.
Target Gene and TIP41-like Gene Detection

| Process | Temp. | Time | No. Cycles |
|---|---|---|---|
| Acquire FAM or HEX | 72° C. | 1 sec | |
| Cool | 40° C. | 10 sec | 1 |

Data are analyzed using LIGHTCYCLER™ Software v1.5 by relative quantification using a second derivative max algorithm for calculation of Cq values according to the supplier's recommendations. For expression analyses, expression values are calculated using the ΔΔCt method (i.e., 2−(Cq TARGET−Cq REF)), which relies on the comparison of differences of Cq values between two targets, with the base value of 2 being selected under the assumption that, for optimized PCR reactions, the product doubles every cycle.

Transcript Size and Integrity:

Northern Blot Assay. In some instances, additional molecular characterization of the transgenic plants is obtained by the use of Northern Blot (RNA blot) analysis to determine the molecular size of the hairpin dsRNA in transgenic plants expressing a hairpin dsRNA.

All materials and equipment are treated with RNaseZAP (AMBION/INVITROGEN) before use. Tissue samples (100 mg to 500 mg) are collected in 2 mL SAFELOCK EPPENDORF tubes, disrupted with a KLECKO™ tissue pulverizer (GARCIA MANUFACTURING, Visalia, Calif.) with three tungsten beads in 1 mL TRIZOL (INVITROGEN) for 5 min, then incubated at room temperature (RT) for 10 min. Optionally, the samples are centrifuged for 10 min at 4° C. at 11,000 rpm and the supernatant is transferred into a fresh 2 mL SAFELOCK EPPENDORF tube. After 200 µL chloroform are added to the homogenate, the tube is mixed by inversion for 2 to 5 min, incubated at RT for 10 minutes, and centrifuged at 12,000×g for 15 min at 4° C. The top phase is transferred into a sterile 1.5 mL EPPENDORF tube, 600 µL of 100% isopropanol are added, followed by incubation at RT for 10 min to 2 hr, and then centrifuged at 12,000×g for 10 min at 4° C. to 25° C. The supernatant is discarded and the RNA pellet is washed twice with 1 mL 70% ethanol, with centrifugation at 7,500×g for 10 min at 4° C. to 25° C. between washes. The ethanol is discarded and the pellet is briefly air dried for 3 to 5 min before resuspending in 50 of nuclease-free water.

Total RNA is quantified using the NANODROP8000® (THERMO-FISHER) and samples are normalized to 5 µg/10 µL. 10 µL of glyoxal (AMBION/INVITROGEN) is then added to each sample. Five to 14 ng of DIG RNA standard marker mix (ROCHE APPLIED SCIENCE, Indianapolis, Ind.) are dispensed and added to an equal volume of glyoxal. Samples and marker RNAs are denatured at 50° C. for 45 min and stored on ice until loading on a 1.25% SEAKEM GOLD agarose (LONZA, Allendale, N.J.) gel in NORTHERNMAX 10× glyoxal running buffer (AMBION/INVITROGEN). RNAs are separated by electrophoresis at 65 volts/30 mA for 2 hours and 15 minutes.

Following electrophoresis, the gel is rinsed in 2×SSC for 5 min and imaged on a GEL DOC station (BIORAD, Hercules, Calif.), then the RNA is passively transferred to a nylon membrane (MILLIPORE) overnight at RT, using 10×SSC as the transfer buffer (20×SSC consists of 3 M sodium chloride and 300 mM trisodium citrate, pH 7.0). Following the transfer, the membrane is rinsed in 2×SSC for 5 minutes, the RNA is UV-crosslinked to the membrane (AGILENT/STRATAGENE), and the membrane is allowed to dry at room temperature for up to 2 days.

The membrane is pre-hybridized in ULTRAHYB™ buffer (AMBION/INVITROGEN) for 1 to 2 hr. The probe consists of a PCR amplified product containing the sequence of interest, (for example, the antisense sequence portion of SEQ ID NO:1, SEQ ID NO:2, or SEQ ID NO:3, as appropriate) labeled with digoxigenin by means of a ROCHE APPLIED SCIENCE DIG procedure. Hybridization in recommended buffer is overnight at a temperature of 60° C. in hybridization tubes. Following hybridization, the blot is subjected to DIG washes, wrapped, exposed to film for 1 to 30 minutes, then the film is developed, all by methods recommended by the supplier of the DIG kit.

Transgene Copy Number Determination.

Maize leaf pieces approximately equivalent to 2 leaf punches are collected in 96-well collection plates (QIAGEN). Tissue disruption is performed with a KLECKO™ tissue pulverizer (GARCIA MANUFACTURING, Visalia, Calif.) in BIOSPRINT96 AP1 lysis buffer (supplied with a BIOSPRINT96 PLANT KIT; QIAGEN) with one stainless steel bead. Following tissue maceration, gDNA is isolated in high throughput format using a BIOSPRINT96 PLANT KIT and a BIOSPRINT96 extraction robot. gDNA is diluted 1:3 DNA:water prior to setting up the qPCR reaction.

qPCR analysis. Transgene detection by hydrolysis probe assay is performed by real-time PCR using a LIGHTCYCLER®480 system. Oligonucleotides to be used in hydrolysis probe assays to detect the target gene (e.g., SEQ ID NO:1, SEQ ID NO:2, or SEQ ID NO:3), the linker sequence (e.g., a loop, SEQ ID NO:78), and/or to detect a portion of the SpecR gene (i.e., the spectinomycin resistance gene borne on the binary vector plasmids; SEQ ID NO:60; SPC1 oligonucleotides in Table 9), are designed using LIGHTCYCLER® PROBE DESIGN SOFTWARE 2.0. Further, oligonucleotides to be used in hydrolysis probe assays to detect a segment of the AAD-1 herbicide tolerance gene (SEQ ID NO:61; GAAD1 oligonucleotides in Table 9) are designed using PRIMER EXPRESS software (APPLIED BIOSYSTEMS). Table 9 shows the sequences of the primers and probes. Assays are multiplexed with reagents for an endogenous maize chromosomal gene (Invertase (SEQ ID NO:62; GENBANK Accession No: U16123; referred to herein as IVR1), which serves as an internal reference sequence to ensure gDNA is present in each assay. For amplification, LIGHTCYCLER®480 PROBES MASTER mix (ROCHE APPLIED SCIENCE) is prepared at 1× final concentration in a 10 µL volume multiplex reaction containing 0.4 µM of each primer and 0.2 µM of each probe (Table 10). A two-step amplification reaction is performed as outlined in Table 11. Fluorophore activation and emission for the FAM- and HEX-labeled probes are as described above; CY5 conjugates are excited maximally at 650 nm and fluoresce maximally at 670 nm.

Cp scores (the point at which the fluorescence signal crosses the background threshold) are determined from the real time PCR data using the fit points algorithm (LIGHTCYCLER® SOFTWARE release 1.5) and the Relative Quant module (based on the ΔΔCt method). Data are handled as described previously (above; RNA qPCR).

TABLE 9

Sequences of primers and probes (with fluorescent conjugate) used for gene copy number determinations and binary vector plasmid backbone detection.

| Name | Sequence |
| --- | --- |
| GAAD1-F | TGTTCGGTTCCCTCTACCAA (SEQ ID NO: 63) |
| GAAD1-R | CAACATCCATCACCTTGACTGA (SEQ ID NO: 64) |
| GAAD1-P (FAM) | CACAGAACCGTCGCTTCAGCAACA (SEQ ID NO: 65) |
| IVR1-F | TGGCGGACGACGACTTGT (SEQ ID NO: 66) |
| IVR1-R | AAAGTTTGGAGGCTGCCGT (SEQ ID NO: 67) |
| IVR1-P (HEX) | CGAGCAGACCGCCGTGTACTTCTACC (SEQ ID NO: 68) |
| SPC1A | CTTAGCTGGATAACGCCAC (SEQ ID NO: 69) |
| SPC1S | GACCGTAAGGCTTGATGAA (SEQ ID NO: 70) |
| TQSPEC (CY5*) | CGAGATTCTCCGCGCTGTAGA (SEQ ID NO: 71) |
| Loop_F | GGAACGAGCTGCTTGCGTAT (SEQ ID NO: 75) |
| Loop_R | CACGGTGCAGCTGATTGATG (SEQ ID NO: 76) |
| Loop_FAM | TCCCTTCCGTAGTCAGAG (SEQ ID NO: 77) |

*CY5 = Cyanine-5

TABLE 10

Reaction components for gene copy number analyses and plasmid backbone detection.

| Component | Amt. (μL) | Stock | Final Conc'n |
| --- | --- | --- | --- |
| 2x Buffer | 5.0 | 2x | 1x |
| Appropriate Forward Primer | 0.4 | 10 μM | 0.4 |
| Appropriate Reverse Primer | 0.4 | 10 μM | 0.4 |
| Appropriate Probe | 0.4 | 5 μM | 0.2 |
| IVR1-Forward Primer | 0.4 | 10 μM | 0.4 |
| IVR1-Reverse Primer | 0.4 | 10 μM | 0.4 |
| IVR1-Probe | 0.4 | 5 μM | 0.2 |
| H$_2$O | 0.6 | NA* | NA |
| gDNA | 2.0 | ND** | ND |
| Total | 10.0 | | |

*NA = Not Applicable
**ND = Not Determined

TABLE 11

Thermocycler conditions for qPCR. Genomic copy number analyses

| Process | Temp. | Time | No. Cycles |
| --- | --- | --- | --- |
| Target Activation | 95° C. | 10 min | 1 |
| Denature | 95° C. | 10 sec | 40 |
| Extend & Acquire FAM, HEX, or CY5 | 60° C. | 40 sec | |
| Cool | 40° C. | 10 sec | 1 |

Example 8: Bioassay of Transgenic Maize

Insect Bioassays. Bioactivity of dsRNA of the subject invention produced in plant cells is demonstrated by bioassay methods. See, e.g., Baum et al. (2007) Nat. Biotechnol. 25(11):1322-1326. One is able to demonstrate efficacy, for example, by feeding various plant tissues or tissue pieces derived from a plant producing an insecticidal dsRNA to target insects in a controlled feeding environment. Alternatively, extracts are prepared from various plant tissues derived from a plant producing the insecticidal dsRNA, and the extracted nucleic acids are dispensed on top of artificial diets for bioassays as previously described herein. The results of such feeding assays are compared to similarly conducted bioassays that employ appropriate control tissues from host plants that do not produce an insecticidal dsRNA, or to other control samples. Growth and survival of target insects on the test diet is reduced compared to that of the control group.

Insect Bioassays with Transgenic Maize Events.

Two western corn rootworm larvae (1 to 3 days old) hatched from washed eggs are selected and placed into each well of the bioassay tray. The wells are then covered with a "PULL N' PEEL" tab cover (BIO-CV-16, BIO-SERV) and placed in a 28° C. incubator with an 18 hr/6 hr light/dark cycle. Nine days after the initial infestation, the larvae are assessed for mortality, which is calculated as the percentage of dead insects out of the total number of insects in each treatment. The insect samples are frozen at −20° C. for two days, then the insect larvae from each treatment are pooled and weighed. The percent of growth inhibition is calculated as the mean weight of the experimental treatments divided by the mean of the average weight of two control well treatments. The data are expressed as a Percent Growth Inhibition (of the negative controls). Mean weights that exceed the control mean weight are normalized to zero.

Insect Bioassays in the Greenhouse.

Western corn rootworm (WCR, *Diabrotica virgifera virgifera* LeConte) eggs are received in soil from CROP CHARACTERISTICS (Farmington, Minn.). WCR eggs are incubated at 28° C. for 10 to 11 days. Eggs are washed from the soil, placed into a 0.15% agar solution, and the concentration is adjusted to approximately 75 to 100 eggs per 0.25 mL aliquot. A hatch plate is set up in a Petri dish with an aliquot of egg suspension to monitor hatch rates.

The soil around the maize plants growing in ROOTRA-NERS® is infested with 150 to 200 WCR eggs. The insects are allowed to feed for 2 weeks, after which time a "Root Rating" is given to each plant. A Node-Injury Scale is utilized for grading, essentially according to Oleson et al. (2005) J. Econ. Entomol. 98:1-8. Plants passing this bioassay, showing reduced injury, are transplanted to 5-gallon pots for seed production. Transplants are treated with insecticide to prevent further rootworm damage and insect release in the greenhouses. Plants are hand pollinated for seed production. Seeds produced by these plants are saved for evaluation at the T$_1$ and subsequent generations of plants.

Transgenic negative control plants are generated by transformation with vectors harboring genes designed to produce a yellow fluorescent protein (YFP). Non-transformed negative control plants are grown from seeds of parental corn varieties from which the transgenic plants were produced. Bioassays are conducted, with negative controls included in each set of plant materials.

Example 9: Transgenic *Zea mays* Comprising Coleopteran Pest Sequences 10-20 transgenic To *Zea mays* plants are generated as described in EXAMPLE 6. A further 10-20 T$_1$ *Zea mays* independent lines expressing hairpin dsRNA for an RNAi construct are obtained for corn rootworm challenge. Hairpin dsRNA comprise a portion of SEQ ID NO:1. Additional hairpin dsRNAs are derived, for example, from coleopteran pest sequences such as, for example, Caf1-180 (U.S. Patent Application Publication No. 2012/0174258), VatpaseC (U.S. Patent Application Publication No. 2012/0174259), Rho1

(U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), ROP (U.S. patent application Ser. No. 14/577,811), RNA polymerase 11140 (U.S. patent application Ser. No. 14/577,854), Dre4 (U.S. patent application Ser. No. 14/705,807), ncm (U.S. Patent Application No. 62/095,487), COPI alpha (U.S. Patent Application No. 62/063,199), COPI beta (U.S. Patent Application No. 62/063,203), COPI gamma (U.S. Patent Application No. 62/063,192), or COPI delta (U.S. Patent Application No. 62/063,216), RNA polymerase II (U.S. Patent Application No. 62/133,214), RNA polymerase 11-215 (U.S. Patent Application No. 62/133,202), RNA polymerase 33 (U.S. Patent Application No. 62/133,210), and spt5 (U.S. Patent Application No. 62/168,613). These are confirmed through RT-PCR or other molecular analysis methods.

Total RNA preparations from selected independent $T_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic Zea mays plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, and viability of feeding coleopteran pests.

In planta delivery of dsRNA, siRNA, or miRNA corresponding to target genes and the subsequent uptake by coleopteran pests through feeding results in down-regulation of the target genes in the coleopteran pest through RNA-mediated gene silencing. When the function of a target gene is important at one or more stages of development, the growth and/or development of the coleopteran pest is affected, and in the case of at least one of WCR, NCR, SCR, MCR, D. balteata LeConte, D. speciosa Germar, D. u. tenella, and D. u. undecimpunctata Mannerheim, leads to failure to successfully infest, feed, and/or develop, or leads to death of the coleopteran pest. The choice of target genes and the successful application of RNAi are then used to control coleopteran pests.

Phenotypic Comparison of Transgenic RNAi Lines and Nontransformed Zea mays.

Target coleopteran pest genes or sequences selected for creating hairpin dsRNA have no similarity to any known plant gene sequence. Hence, it is not expected that the production or the activation of (systemic) RNAi by constructs targeting these coleopteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are recorded. In general, there are no observable morphological differences between transgenic lines and those without expression of target iRNA molecules when cultured in vitro and in soil in the glasshouse.

Example 10: Transgenic Zea mays Comprising a Coleopteran Pest Sequence and Additional RNAi Constructs A transgenic Zea mays plant comprising a heterologous coding sequence in its genome that is transcribed into an iRNA molecule that targets an organism other than a coleopteran pest is secondarily transformed via Agrobacterium or WHISKERS™ methodologies (see Petolino and Arnold (2009) Methods Mol. Biol. 526:59-67) to produce one or more insecticidal dsRNA molecules (for example, at least one dsRNA molecule including a dsRNA molecule targeting a gene comprising SEQ ID NO:1). Plant transformation plasmid vectors prepared essentially as described in EXAMPLE 4 are delivered via Agrobacterium or WHISKERS™-mediated transformation methods into maize suspension cells or immature maize embryos obtained from a transgenic Hi II or B104 Zea mays plant comprising a heterologous coding sequence in its genome that is transcribed into an iRNA molecule that targets an organism other than a coleopteran pest.

Example 11: Transgenic Zea mays Comprising an RNAi Construct and Additional Coleopteran Pest Control Sequences A transgenic Zea mays plant comprising a heterologous coding sequence in its genome that is transcribed into an iRNA molecule that targets a coleopteran pest organism (for example, at least one dsRNA molecule including a dsRNA molecule targeting a gene comprising SEQ ID NO:1) is secondarily transformed via Agrobacterium or WHISKERS™ methodologies (see Petolino and Arnold (2009) Methods Mol. Biol. 526:59-67) to produce one or more insecticidal protein molecules, for example, Cry3, Cry34 Cry35, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C insecticidal proteins. Plant transformation plasmid vectors prepared essentially as described in EXAMPLE 4 are delivered via Agrobacterium or WHISKERS™-mediated transformation methods into maize suspension cells or immature maize embryos obtained from a transgenic B104 Zea mays plant comprising a heterologous coding sequence in its genome that is transcribed into an iRNA molecule that targets a coleopteran pest organism. Doubly-transformed plants are obtained that produce iRNA molecules and insecticidal proteins for control of coleopteran pests.

Example 12: dsRNA in Insect Management dsRNA transgenes targeting SEQ ID NO:1, SEQ ID NO:2, or SEQ ID NO:3 are combined with other dsRNA molecules in transgenic plants to provide redundant RNAi targeting and synergistic RNAi effects. Transgenic plants including, for example and without limitation, corn expressing dsRNA that targets SEQ ID NO:1, SEQ ID NO:2, or SEQ ID NO:3 are useful for preventing feeding damage by coleopteran insects. These dsRNA transgenes are also combined in plants with *Bacillus thuringiensis* insecticidal protein technology to represent new modes of action in Insect Resistance Management gene pyramids. When combined with other dsRNA molecules that target insect pests and/or with insecticidal proteins in transgenic plants, a synergistic insecticidal effect is observed that also mitigates the development of resistant insect populations.

What is claimed is:

1. An isolated nucleic acid molecule comprising a polynucleotide operably linked to a heterologous promoter, wherein the polynucleotide encodes a hairpin ribonucleic acid (hpRNA) molecule with a stem and a loop structure that kills WCR with an $LC_{50}$ of less than 15 ng/cm$^2$ when ingested by the insect, the polynucleotide comprising:
   a sense nucleotide sequence that comprises SEQ ID NO:3; and
   the antisense nucleotide sequence of SEQ ID NO:3, wherein the sense nucleotide sequence and the antisense nucleotide sequence encode ribonucleotide sequences in the stem structure of the hpRNA molecule, the polynucleotide further comprising:
   a spacer nucleotide sequence comprising SEQ ID NO:78 between the sense and antisense nucleotide sequences, wherein the loop structure of the hpRNA molecule comprises the ribonucleotide sequence encoded by the spacer nucleotide sequence.

2. An hpRNA molecule encoded by the polynucleotide of the nucleic acid molecule of claim 1, wherein the hpRNA molecule kills WCR when ingested by the insect.

3. The nucleic acid molecule of claim 1, wherein the promoter is functional in a plant cell.

4. A prokaryotic cell comprising the nucleic acid molecule of claim 1.

5. A eukaryotic cell comprising the nucleic acid molecule of claim 1.

6. A transgenic plant cell comprising the nucleic acid molecule of claim 3.

7. A plant comprising the hpRNA molecule of claim 2.

8. A transgenic plant commodity product comprising a detectable amount of the polynucleotide of the nucleic acid molecule of claim 1.

9. A transgenic plant or seed thereof comprising the nucleic acid molecule of claim 3, wherein the heterologous promoter is functional in the plant.

10. The transgenic plant or seed thereof of claim 9, wherein the plant is Zea mays.

11. A method for controlling a Diabrotica virgifera insect population, the method comprising feeding insects of the population with the hpRNA molecule of claim 2.

12. The method according to claim 11, wherein the agent is a sprayable formulation.

13. A method for controlling a Diabrotica virgifera insect population, the method comprising feeding insects of the population with plant material from a transgenic Diabrotica virgifera host plant comprising the nucleic acid molecule of claim 3, wherein the hpRNA molecule is expressed in the plant material.

14. A method for producing a transgenic plant cell, the method comprising:
   transforming a plant cell with the nucleic acid molecule of claim 3;
   culturing the transformed plant cell under conditions sufficient to allow for development of a plant cell culture comprising a plurality of plant cells comprising the polynucleotide; and
   selecting a transgenic plant cell that has integrated the polynucleotide into its genome, and that expresses the hpRNA molecule.

15. The nucleic acid molecule of claim 1, further comprising a polynucleotide encoding an insecticidal polypeptide from Bacillus thuringiensis, Alcaligenes spp., or Pseudomonas spp.

16. The nucleic acid molecule of claim 15, wherein the insecticidal polypeptide is from B. thuringiensis, and is selected from the group consisting of Cry1B, Cry3, Cry34, Cry35, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

17. The transgenic plant or seed thereof of claim 9, wherein the plant or seed thereof comprises a polynucleotide encoding an insecticidal polypeptide from Bacillus thuringiensis, Alcaligenes spp., or Pseudomonas spp.

18. The transgenic plant or seed thereof of claim 17, wherein the insecticidal polypeptide is from *B. thuringiensis*, and is selected from the group consisting of Cry1B, Cry3, Cry34, Cry35, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

19. The plant of claim 7, wherein the plant comprises an insecticidal polypeptide from *Bacillus thuringiensis, Alcaligenes* spp., or *Pseudomonas* spp.

20. The plant of claim 19, wherein the insecticidal polypeptide is from *B. thuringiensis*, and is selected from the group consisting of Cry1B, Cry3, Cry34, Cry35, Cry 1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

21. The method according to claim 11, wherein the method further comprises feeding insects of the population with an insecticidal polypeptide from *Bacillus thuringiensis, Alcaligenes* spp., or *Pseudomonas* spp.

22. The method according to claim 21, wherein the insecticidal polypeptide is from *B. thuringiensis*, and is selected from the group consisting of Cry1B, Cry3, Cry34, Cry35, Cry 1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

23. A method for producing a transgenic plant, the method comprising:
    regenerating a transgenic plant from the transgenic plant cell of claim 6.

24. The plant of claim 7, wherein the plant is a transgenic plant expressing the hpRNA molecule.

25. The transgenic plant of claim 24, wherein the plant is *Zea mays*.

26. A method for improving the yield of a corn crop, the method comprising:
    cultivating in the corn crop the transgenic plant or seed thereof of claim 9.

27. A plant material comprising the hpRNA molecule of claim 2.

28. The plant material of claim 27, wherein the plant material is a transgenic plant material expressing the hpRNA molecule.

29. The transgenic plant material of claim 28, wherein the plant material is a *Zea mays* plant material.

30. A transgenic plant material comprising the nucleic acid molecule of claim 3.

31. The transgenic plant material of claim 30, wherein the plant material is a seed.

* * * * *

```
                              SEQUENCE LISTING

<160> NUMBER OF SEQ ID NOS: 81

<210> SEQ ID NO 1
<211> LENGTH: 499
<212> TYPE: DNA
<213> ORGANISM: Diabrotica virgifera

<400> SEQUENCE: 1
cgccttacac tccaagtggt caaactccat acatgactcc gtacgctaca ccccatacgc        60
agcaaactcc ccgctatggt catcaaacac cttcccaaca catggcgagc tcagcaccac       120
aaggtctcaa caatcccttt ttacatcctg gcgcggtgac tccctcccaa cgaactccta       180
tttatcgcaa ccatcctgca caatctccag taatgcttcc tacaagccct gtaccaagtc       240
caggttccca gagttcatac agtagtcatt taagtcataa tcagcgaagt ggaagttatg       300
ctgaatcctt aagattccaa cctcccgaat cgccgagaag ctcagtgagt aatagaagct       360
ttcaaactga tagatacggc ggtgataggt atggtaaagg aggaagtcat agatatggtg       420
gaagctcaaa cgaagataga tatggtaagg gaggaggagg aaatgaaaat acggattggc       480
agaaagctgc agaagcatg                                                   499

<210> SEQ ID NO 2
<211> LENGTH: 145
<212> TYPE: DNA
<213> ORGANISM: Diabrotica virgifera

<400> SEQUENCE: 2
gactccgtac gctacacccc atacgcagca aactccccgc tatggtcatc aaacaccttc        60
ccaacacatg gcgagctcag caccacaagg tctcaacaat ccctttttac atcctggcgc       120
ggtgactccc tcccaacgaa ctcct                                             145

<210> SEQ ID NO 3
<211> LENGTH: 108
<212> TYPE: DNA
<213> ORGANISM: Diabrotica virgifera

<400> SEQUENCE: 3
agagttcata cagtagtcat ttaagtcata atcagcgaag tggaagttat gctgaatcct        60
taagattcca acctcccgaa tcgccgagaa gctcagtgag taatagaa                    108

<210> SEQ ID NO 4
<211> LENGTH: 24
<212> TYPE: DNA
<213> ORGANISM: Artificial Sequence
<220> FEATURE:
<223> OTHER INFORMATION: T7 phage promoter

<400> SEQUENCE: 4
ttaatacgac tcactatagg gaga                                               24

<210> SEQ ID NO 5
<211> LENGTH: 503
<212> TYPE: DNA
<213> ORGANISM: Artificial Sequence
<220> FEATURE:
<223> OTHER INFORMATION: Partial YFP coding sequence
```

```
<400> SEQUENCE: 5
caccatgggc tccagcggcg ccctgctgtt ccacggcaag atcccctacg tggtggagat        60
ggagggcaat gtggatggcc acaccttcag catccgcggc aagggctacg gcgatgccag       120
cgtgggcaag gtggatgccc agttcatctg caccaccggc gatgtgcccg tgccctggag       180
caccctggtg accaccctga cctacggcgc ccagtgcttc gccaagtacg gccccgagct       240
gaaggatttc tacaagagct gcatgcccga tggctacgtg caggagcgca ccatcacctt       300
cgagggcgat ggcaatttca gacccgcgc cgaggtgacc ttcgagaatg cagcgtgta        360 caatcgcgtg aagctgaatg ccagggctt caagaaggat ggccacgtgc tgggcaagaa       420
tctggagttc aatttcaccc cccactgcct gtacatctgg ggcgatcagg ccaatcacgg       480
cctgaagagc gccttcaaga tct                                               503

<210> SEQ ID NO 6
<211> LENGTH: 49
<212> TYPE: DNA
<213> ORGANISM: Artificial Sequence
<220> FEATURE:
<223> OTHER INFORMATION: Primer Dvv-tg-1_For

<400> SEQUENCE: 6
ttaatacgac tcactatagg gagacgcctt acactccaag tggtcaaac                    49

<210> SEQ ID NO 7
<211> LENGTH: 50
<212> TYPE: DNA
<213> ORGANISM: Artificial Sequence
<220> FEATURE:
<223> OTHER INFORMATION: Primer Dvv-tg-1_Rev

<400> SEQUENCE: 7
ttaatacgac tcactatagg gagacatgct tctgcagctt tctgccaatc                   50

<210> SEQ ID NO 8
<211> LENGTH: 48
<212> TYPE: DNA
<213> ORGANISM: Artificial Sequence
<220> FEATURE:
<223> OTHER INFORMATION: Primer Dvv-tg-1_v1_For

<400> SEQUENCE: 8
ttaatacgac tcactatagg gagagactcc gtacgctaca ccccatac                     48

<210> SEQ ID NO 9
<211> LENGTH: 48
<212> TYPE: DNA
<213> ORGANISM: Artificial Sequence
<220> FEATURE:
<223> OTHER INFORMATION: Primer Dvv-tg-1_v1_Rev

<400> SEQUENCE: 9
ttaatacgac tcactatagg gagaaggagt tcgttgggag ggagtcac                     48

<210> SEQ ID NO 10
<211> LENGTH: 51
<212> TYPE: DNA
<213> ORGANISM: Artificial Sequence
<220> FEATURE:
<223> OTHER INFORMATION: Primer Dvv-tg-1_v2_For

<400> SEQUENCE: 10
```
ttaatacgac tcactatagg gagaagagtt catacagtag tcatttaagt c        51

<210> SEQ ID NO 11
<211> LENGTH: 48
<212> TYPE: DNA
<213> ORGANISM: Artificial Sequence
<220> FEATURE:
<223> OTHER INFORMATION: Primer Dvv-tg-1_v2_Rev

<400> SEQUENCE: 11
ttaatacgac tcactatagg gagattctat tactcactga gcttctcg          48

<210> SEQ ID NO 12
<211> LENGTH: 705
<212> TYPE: DNA
<213> ORGANISM: Artificial Sequence
<220> FEATURE:
<223> OTHER INFORMATION: Synthetic YFP coding sequence

<400> SEQUENCE: 12
atgtcatctg agcacttct cttcatggg aagattcctt acgttgtgga gatggaaggg    60
aatgttgatg ccacaccttt agcatacgt gggaaaggct acggagatgc ctcagtggga   120
aaggttgatg cacagttcat ctgcacaact ggtgatgttc ctgtgccttg gagcacactt   180
gtcaccactc tcacctatgg agcacagtgc tttgccaagt atggtccaga gttgaaggac   240
ttctacaagt cctgtatgcc agatggctat gtgcaagagc gcacaatcac ctttgaagga   300
gatggcaact tcaagactag ggctgaagtc acctttgaga tgggtctgt ctacaatagg    360 gtcaaactca atggtcaagg cttcaagaaa gatggtcatg tgttgggaaa gaacttggag   420
ttcaacttca ctccccactg cctctacatc tggggtgacc aagccaacca cggtctcaag   480
tcagccttca gatctgtca tgagattact ggcagcaaag gcgacttcat agtggctgac   540
cacacccaga tgaacactcc cattggtgga ggtccagttc atgttccaga gtatcatcac   600
atgtcttacc atgtgaaact ttccaaagat gtgacagacc acagacaa catgtccttg    660 aaagaaactg tcagagctgt tgactgtcgc aagacctacc tttga                705

<210> SEQ ID NO 13
<211> LENGTH: 218
<212> TYPE: DNA
<213> ORGANISM: Diabrotica virgifera

<400> SEQUENCE: 13
tagctctgat gacagagccc atcgagtttc aagccaaaca gttgcataaa gctatcagcg    60
gattgggaac tgatgaaagt acaatmgtmg aaattttaag tgtmcacaac aacgatgaga   120
ttataagaat ttcccaggcc tatgaaggat tgtaccaacg mtcattggaa tctgatatca   180
aaggagatac ctcaggaaca ttaaaaaaga attattag                          218

<210> SEQ ID NO 14
<211> LENGTH: 424
<212> TYPE: DNA
<213> ORGANISM: Diabrotica virgifera
<220> FEATURE:
<221> NAME/KEY: misc_feature
<222> LOCATION: (393)..(395)
<223> OTHER INFORMATION: n is a, c, g, or t

<400> SEQUENCE: 14
ttgttacaag ctggagaact tctctttgct ggaaccgaag agtcagtatt taatgctgta    60
ttctgtcaaa gaaataaacc acaattgaat ttgatattcg acaaatatga agaaattgtt   120

```
gggcatccca ttgaaaaagc cattgaaaac gagttttcag gaaatgctaa acaagccatg    180
ttacacctta tccagagcgt aagagatcaa gttgcatatt tggtaaccag gctgcatgat    240
tcaatggcag gcgtcggtac tgacgataga actttaatca gaattgttgt ttcgagatct    300
gaaatcgatc tagaggaaat caaacaatgc tatgaagaaa tctacagtaa aaccttggct    360
gataggatag cggatgacac atctggcgac tannnaaaag ccttattagc cgttgttggt    420
taag                                                                 424
```

<210> SEQ ID NO 15
<211> LENGTH: 397
<212> TYPE: DNA
<213> ORGANISM: Diabrotica virgifera

<400> SEQUENCE: 15

```
agatgttggc tgcatctaga gaattacaca agttcttcca tgattgcaag gatgtactga     60
gcagaatagt ggaaaaacag gtatccatgt ctgatgaatt gggaagggac gcaggagctg    120
tcaatgccct tcaacgcaaa caccagaact tcctccaaga cctacaaaca ctccaatcga    180
acgtccaaca aatccaagaa gaatcagcta aacttcaagc tagctatgcc ggtgatagag    240
ctaaagaaat caccaacagg gagcaggaag tggtagcagc ctgggcagcc ttgcagatcg    300
cttgcgatca gagacacgga aaattgagcg atactggtga tctattcaaa ttctttaact    360
tggtacgaac gttgatgcag tggatggacg aatggac                             397
```

<210> SEQ ID NO 16
<211> LENGTH: 490
<212> TYPE: DNA
<213> ORGANISM: Diabrotica virgifera

<400> SEQUENCE: 16

```
gcagatgaac accagcgaga aaccaagaga tgttagtggt gttgaattgt tgatgaacaa     60
ccatcagaca ctcaaggctg agatcgaagc cagagaagac aactttacgg cttgtatttc    120
tttaggaaag gaattgttga gccgtaatca ctatgctagt gctgatatta aggataaatt    180
ggtcgcgttg acgaatcaaa ggaatgctgt actacagagg tgggaagaaa gatgggagaa    240
cttgcaactc atcctcgagg tataccaatt cgccagagat gcggccgtcg ccgaagcatg    300
gttgatcgca caagaacctt acttgatgag ccaagaacta ggacacacca ttgacgacgt    360
tgaaaacttg ataaagaaac acgaagcgtt cgaaaaatcg gcagcggcgc aagaagagag    420
attcagtgct ttggagagac tgacgacgtt cgaattgaga gaaataaaga ggaaacaaga    480
agctgcccag                                                           490
```

<210> SEQ ID NO 17
<211> LENGTH: 330
<212> TYPE: DNA
<213> ORGANISM: Diabrotica virgifera

<400> SEQUENCE: 17

```
agtgaaatgt tagcaaatat aacatccaag tttcgtaatt gtacttgctc agttagaaaa     60
tattctgtag tttcactatc ttcaaccgaa aatagaataa atgtagaacc tcgcgaactt    120
gcctttcctc caaaatatca agaacctcga caagtttggt tggagagttt agatacgata    180
gacgacaaaa aattgggtat tcttgagctg catcctgatg ttttttgctac taatccaaga    240 atagatatta tacatcaaaa tgttagatgg caaagtttat atagatatgt aagctatgct    300
```
catacaaagt caagatttga agtgagaggt      330

<210> SEQ ID NO 18
<211> LENGTH: 320
<212> TYPE: DNA
<213> ORGANISM: Diabrotica virgifera

<400> SEQUENCE: 18
caaagtcaag atttgaagtg agaggtggag gtcgaaaacc gtggccgcaa aagggattgg      60
gacgtgctcg acatggttca attagaagtc cactttggag aggtggagga gttgttcatg      120
gaccaaaatc tccaacccct cattttttaca tgattccatt ctacacccgt ttgctgggtt      180
tgactagcgc actttcagta aaatttgccc aagatgactt gcacgttgtg gatagtctag      240
atctgccaac tgacgaacaa agttatatag aagagctggt caaaagccgc ttttgggggt      300
ccttcttgtt ttatttgtag      320

<210> SEQ ID NO 19
<211> LENGTH: 47
<212> TYPE: DNA
<213> ORGANISM: Artificial Sequence
<220> FEATURE:
<223> OTHER INFORMATION: Primer YFP-F_T7

<400> SEQUENCE: 19
ttaatacgac tcactatagg gagacaccat gggctccagc ggcgccc      47

<210> SEQ ID NO 20
<211> LENGTH: 23
<212> TYPE: DNA
<213> ORGANISM: Artificial Sequence
<220> FEATURE:
<223> OTHER INFORMATION: Primer YFP-R

<400> SEQUENCE: 20
agatcttgaa ggcgctcttc agg      23

<210> SEQ ID NO 21
<211> LENGTH: 23
<212> TYPE: DNA
<213> ORGANISM: Artificial Sequence
<220> FEATURE:
<223> OTHER INFORMATION: Primer YFP-F

<400> SEQUENCE: 21
caccatgggc tccagcggcg ccc      23

<210> SEQ ID NO 22
<211> LENGTH: 47
<212> TYPE: DNA
<213> ORGANISM: Artificial Sequence
<220> FEATURE:
<223> OTHER INFORMATION: Primer YFP-R_T7

<400> SEQUENCE: 22
ttaatacgac tcactatagg gagaagatct tgaaggcgct cttcagg      47

<210> SEQ ID NO 23
<211> LENGTH: 46
<212> TYPE: DNA
<213> ORGANISM: Artificial Sequence
<220> FEATURE:
<223> OTHER INFORMATION: Primer Ann-F1_T7

<400> SEQUENCE: 23
ttaatacgac tcactatagg gagagctcca acagtggttc cttatc        46

<210> SEQ ID NO 24
<211> LENGTH: 29
<212> TYPE: DNA
<213> ORGANISM: Artificial Sequence
<220> FEATURE:
<223> OTHER INFORMATION: Primer Ann-R1

<400> SEQUENCE: 24
ctaataattc ttttttaatg ttcctgagg        29

<210> SEQ ID NO 25
<211> LENGTH: 22
<212> TYPE: DNA
<213> ORGANISM: Artificial Sequence
<220> FEATURE:
<223> OTHER INFORMATION: Primer Ann-F1

<400> SEQUENCE: 25
gctccaacag tggttcctta tc        22

<210> SEQ ID NO 26
<211> LENGTH: 53
<212> TYPE: DNA
<213> ORGANISM: Artificial Sequence
<220> FEATURE:
<223> OTHER INFORMATION: Primer Ann-R1_T7

<400> SEQUENCE: 26
ttaatacgac tcactatagg gagactaata attcttttt aatgttcctg agg        53

<210> SEQ ID NO 27
<211> LENGTH: 48
<212> TYPE: DNA
<213> ORGANISM: Artificial Sequence
<220> FEATURE:
<223> OTHER INFORMATION: Primer Ann-F2_T7

<400> SEQUENCE: 27
ttaatacgac tcactatagg gagattgtta caagctggag aacttctc        48

<210> SEQ ID NO 28
<211> LENGTH: 24
<212> TYPE: DNA
<213> ORGANISM: Artificial Sequence
<220> FEATURE:
<223> OTHER INFORMATION: Primer Ann-R2

<400> SEQUENCE: 28
cttaaccaac aacggctaat aagg        24

<210> SEQ ID NO 29
<211> LENGTH: 24
<212> TYPE: DNA
<213> ORGANISM: Artificial Sequence
<220> FEATURE:
<223> OTHER INFORMATION: Primer Ann-F2

<400> SEQUENCE: 29
ttgttacaag ctggagaact ctc        24

<210> SEQ ID NO 30
<211> LENGTH: 48
<212> TYPE: DNA

<213> ORGANISM: Artificial Sequence
<220> FEATURE:
<223> OTHER INFORMATION: Primer Ann-R2T7

<400> SEQUENCE: 30
ttaatacgac tcactatagg gagacttaac caacaacggc taataagg            48

<210> SEQ ID NO 31
<211> LENGTH: 47
<212> TYPE: DNA
<213> ORGANISM: Artificial Sequence
<220> FEATURE:
<223> OTHER INFORMATION: Primer Betasp2-F1_T7

<400> SEQUENCE: 31
ttaatacgac tcactatagg gagaagatgt tggctgcatc tagagaa             47

<210> SEQ ID NO 32
<211> LENGTH: 22
<212> TYPE: DNA
<213> ORGANISM: Artificial Sequence
<220> FEATURE:
<223> OTHER INFORMATION: Primer Betasp2-R1

<400> SEQUENCE: 32
gtccattcgt ccatccactg ca                                        22

<210> SEQ ID NO 33
<211> LENGTH: 23
<212> TYPE: DNA
<213> ORGANISM: Artificial Sequence
<220> FEATURE:
<223> OTHER INFORMATION: Primer Betasp2-F1

<400> SEQUENCE: 33
agatgttggc tgcatctaga gaa                                       23

<210> SEQ ID NO 34
<211> LENGTH: 46
<212> TYPE: DNA
<213> ORGANISM: Artificial Sequence
<220> FEATURE:
<223> OTHER INFORMATION: Primer Betasp2-R1_T7

<400> SEQUENCE: 34
ttaatacgac tcactatagg gagagtccat tcgtccatcc actgca              46

<210> SEQ ID NO 35
<211> LENGTH: 46
<212> TYPE: DNA
<213> ORGANISM: Artificial Sequence
<220> FEATURE:
<223> OTHER INFORMATION: Primer Betasp2-F2_T7

<400> SEQUENCE: 35
ttaatacgac tcactatagg gagagcagat gaacaccagc gagaaa              46

<210> SEQ ID NO 36
<211> LENGTH: 22
<212> TYPE: DNA
<213> ORGANISM: Artificial Sequence
<220> FEATURE:
<223> OTHER INFORMATION: Primer Betasp2-R2

<400> SEQUENCE: 36
ctgggcagct tcttgtttcc tc                                        22

<210> SEQ ID NO 37
<211> LENGTH: 22
<212> TYPE: DNA
<213> ORGANISM: Artificial Sequence
<220> FEATURE:
<223> OTHER INFORMATION: Primer Betasp2-F2

<400> SEQUENCE: 37
gcagatgaac accagcgaga aa                                              22

<210> SEQ ID NO 38
<211> LENGTH: 46
<212> TYPE: DNA
<213> ORGANISM: Artificial Sequence
<220> FEATURE:
<223> OTHER INFORMATION: Primer Betasp2-R2_T7

<400> SEQUENCE: 38
ttaatacgac tcactatagg gagactgggc agcttcttgt ttcctc                    46

<210> SEQ ID NO 39
<211> LENGTH: 51
<212> TYPE: DNA
<213> ORGANISM: Artificial Sequence
<220> FEATURE:
<223> OTHER INFORMATION: Primer L4-F1_T7

<400> SEQUENCE: 39
ttaatacgac tcactatagg gagaagtgaa atgttagcaa atataacatc c              51

<210> SEQ ID NO 40
<211> LENGTH: 26
<212> TYPE: DNA
<213> ORGANISM: Artificial Sequence
<220> FEATURE:
<223> OTHER INFORMATION: Primer L4-R1

<400> SEQUENCE: 40
acctctcact tcaaatcttg actttg                                          26

<210> SEQ ID NO 41
<211> LENGTH: 27
<212> TYPE: DNA
<213> ORGANISM: Artificial Sequence
<220> FEATURE:
<223> OTHER INFORMATION: Primer L4-F1

<400> SEQUENCE: 41
agtgaaatgt tagcaaatat aacatcc                                         27

<210> SEQ ID NO 42
<211> LENGTH: 50
<212> TYPE: DNA
<213> ORGANISM: Artificial Sequence
<220> FEATURE:
<223> OTHER INFORMATION: Primer L4-R1_T7

<400> SEQUENCE: 42
ttaatacgac tcactatagg gagaacctct cacttcaaat cttgactttg                50

<210> SEQ ID NO 43
<211> LENGTH: 50
<212> TYPE: DNA
<213> ORGANISM: Artificial Sequence
<220> FEATURE:

<223> OTHER INFORMATION: Primer L4-F2_T7

<400> SEQUENCE: 43
ttaatacgac tcactatagg gagacaaagt caagatttga agtgagaggt         50

<210> SEQ ID NO 44
<211> LENGTH: 25
<212> TYPE: DNA
<213> ORGANISM: Artificial Sequence
<220> FEATURE:
<223> OTHER INFORMATION: Primer L4-R2

<400> SEQUENCE: 44
ctacaaataa aacaagaagg acccc                                    25

<210> SEQ ID NO 45
<211> LENGTH: 26
<212> TYPE: DNA
<213> ORGANISM: Artificial Sequence
<220> FEATURE:
<223> OTHER INFORMATION: Primer L4-F2

<400> SEQUENCE: 45
caaagtcaag atttgaagtg agaggt                                   26

<210> SEQ ID NO 46
<211> LENGTH: 49
<212> TYPE: DNA
<213> ORGANISM: Artificial Sequence
<220> FEATURE:
<223> OTHER INFORMATION: Primer L4-R2_T7

<400> SEQUENCE: 46
ttaatacgac tcactatagg gagactacaa ataaacaag aaggacccc            49

<210> SEQ ID NO 47
<211> LENGTH: 1150
<212> TYPE: DNA
<213> ORGANISM: Zea mays

<400> SEQUENCE: 47
caacggggca gcactgcact gcactgcaac tgcgaatttc cgtcagcttg gagcggtcca    60
agcgccctgc gaagcaaact acgccgatgg cttcggcggc ggcgtgggag ggtccgacgg   120
ccgcggagct gaagacagcg ggggcggagg tgattcccgg cggcgtgcga gtgaaggggt   180
gggtcatcca gtcccacaaa ggccctatcc tcaacgccgc ctctctgcaa cgctttgaag   240
atgaacttca aacaacacat ttacctgaga tggttttgg agagagtttc ttgtcacttc    300
aacatacaca aactggcatc aaatttcatt ttaatgcgct tgatgcactc aaggcatgga   360
agaaagaggc actgccacct gttgaggttc ctgctgcagc aaaatggaag ttcagaagta   420
agccttctga ccaggttata cttgactacg actatacatt tacgacacca tattgtggga   480
gtgatgctgt ggttgtgaac tctggcactc cacaaacaag tttagatgga tgcggcactt   540
tgtgttggga ggatactaat gatcggattg acattgttgc cctttcagca aaagaaccca   600
ttcttttcta cgacgaggtt atcttgtatg aagatgagtt agctgacaat ggtatctcat   660
ttcttactgt gcgagtgagg gtaatgccaa ctggttggtt tctgcttttg cgttttggc    720
ttagagttga tggtgtactg atgaggttga gagacactcg gttacattgc ctgtttggaa   780
acggcgacgg agccaagcca gtggtacttc gtgagtgctg ctggagggaa gcaacatttg   840
ctactttgtc tgcgaaagga tatccttcgg actctgcagc gtacgcggac ccgaacctta   900
ttgcccataa gcttcctatt gtgacgcaga agacccaaaa gctgaaaaat cctacctgac    960
tgacacaaag gcgccctacc gcgtgtacat catgactgtc ctgtcctatc gttgccttt    1020 gtgtttgcca catgttgtgg atgtacgttt ctatgacgaa acaccatagt ccatttcgcc   1080
tgggccgaac agagatagct gattgtcatg tcacgtttga attagaccat tccttagccc   1140
tttttccccc                                                          1150

<210> SEQ ID NO 48
<211> LENGTH: 22
<212> TYPE: DNA
<213> ORGANISM: Artificial Sequence
<220> FEATURE:
<223> OTHER INFORMATION: Oligonucleotide T20VN
<220> FEATURE:
<221> NAME/KEY: misc_feature
<222> LOCATION: (22)..(22)
<223> OTHER INFORMATION: n is a, c, g, or t

<400> SEQUENCE: 48
tttttttttt tttttttttt vn                                              22

<210> SEQ ID NO 49
<211> LENGTH: 20
<212> TYPE: DNA
<213> ORGANISM: Artificial Sequence
<220> FEATURE:
<223> OTHER INFORMATION: Primer P5U76S (F)

<400> SEQUENCE: 49
ttgtgatgtt ggtggcgtat                                                 20

<210> SEQ ID NO 50
<211> LENGTH: 24
<212> TYPE: DNA
<213> ORGANISM: Artificial Sequence
<220> FEATURE:
<223> OTHER INFORMATION: Primer P5U76A (R)

<400> SEQUENCE: 50
tgttaaataa aaccccaaag atcg                                            24

<210> SEQ ID NO 51
<211> LENGTH: 21
<212> TYPE: DNA
<213> ORGANISM: Artificial Sequence
<220> FEATURE:
<223> OTHER INFORMATION: Primer TIPmxF

<400> SEQUENCE: 51
tgagggtaat gccaactggt t                                               21

<210> SEQ ID NO 52
<211> LENGTH: 24
<212> TYPE: DNA
<213> ORGANISM: Artificial Sequence
<220> FEATURE:
<223> OTHER INFORMATION: Primer TIPmxR

<400> SEQUENCE: 52
gcaatgtaac cgagtgtctc tcaa                                            24

<210> SEQ ID NO 53
<211> LENGTH: 32
<212> TYPE: DNA

```
<213> ORGANISM: Artificial Sequence
<220> FEATURE:
<223> OTHER INFORMATION: Probe HXTIP

<400> SEQUENCE: 53
tttttggctt agagttgatg gtgtactgat ga                    32

<210> SEQ ID NO 54
<211> LENGTH: 20
<212> TYPE: DNA
<213> ORGANISM: Artificial Sequence
<220> FEATURE:
<223> OTHER INFORMATION: Primer tg1v1_360 R

<400> SEQUENCE: 54
ggaaatacgc aagcagctcg                                  20

<210> SEQ ID NO 55
<211> LENGTH: 20
<212> TYPE: DNA
<213> ORGANISM: Artificial Sequence
<220> FEATURE:
<223> OTHER INFORMATION: Probe tg1v1_224 P

<400> SEQUENCE: 55
catcctggcg cggtgactcc                                  20

<210> SEQ ID NO 56
<211> LENGTH: 20
<212> TYPE: DNA
<213> ORGANISM: Artificial Sequence
<220> FEATURE:
<223> OTHER INFORMATION: Primer tg1v1_62 F

<400> SEQUENCE: 56
aagatcctgc ctgaacctgc                                  20

<210> SEQ ID NO 57
<211> LENGTH: 20
<212> TYPE: DNA
<213> ORGANISM: Artificial Sequence
<220> FEATURE:
<223> OTHER INFORMATION: Primer tg1v2_323 R

<400> SEQUENCE: 57
ggaaatacgc aagcagctcg                                  20

<210> SEQ ID NO 58
<211> LENGTH: 20
<212> TYPE: DNA
<213> ORGANISM: Artificial Sequence
<220> FEATURE:
<223> OTHER INFORMATION: Probe tg1v2_182 P

<400> SEQUENCE: 58
ccaacctccc gaatcgccga                                  20

<210> SEQ ID NO 59
<211> LENGTH: 20
<212> TYPE: DNA
<213> ORGANISM: Artificial Sequence
<220> FEATURE:
<223> OTHER INFORMATION: Primer tg1v2_86 F

<400> SEQUENCE: 59
tcctgcaaga acgtgggtac                                  20
```

<210> SEQ ID NO 60
<211> LENGTH: 151
<212> TYPE: DNA
<213> ORGANISM: Escherichia coli

<400> SEQUENCE: 60
gaccgtaagg cttgatgaaa caacgcggcg agctttgatc aacgaccttt tggaaacttc     60
ggcttcccct ggagagagcg agattctccg cgctgtagaa gtcaccattg ttgtgcacga    120
cgacatcatt ccgtggcgtt atccagctaa g                                   151

<210> SEQ ID NO 61
<211> LENGTH: 69
<212> TYPE: DNA
<213> ORGANISM: Artificial Sequence
<220> FEATURE:
<223> OTHER INFORMATION: Portion of AAD1 coding region

<400> SEQUENCE: 61
tgttcggttc cctctaccaa gcacagaacc gtcgcttcag caacacctca gtcaaggtga     60
tggatgttg                                                             69

<210> SEQ ID NO 62
<211> LENGTH: 4233
<212> TYPE: DNA
<213> ORGANISM: Zea mays

<400> SEQUENCE: 62
agcctggtgt ttccggagga gacagacatg atccctgccg ttgctgatcc gacgacgctg     60
gacggcgggg gcgcgcgcag gccgttgctc ccggagacgg accctcgggg gcgtgctgcc    120
gccggcgccg agcagaagcg gccgccggct acgccgaccg ttctcaccgc cgtcgtctcc    180
gccgtgctcc tgctcgtcct cgtggcggtc acagtcctcg cgtcgcagca cgtcgacggg    240
caggctgggg gcgttcccgc gggcgaagat gccgtcgtcg tcgaggtggc cgcctcccgt    300
ggcgtggctg agggcgtgtc ggagaagtcc acggccccgc tcctcggctc cggcgcgctc    360
caggacttct cctggaccaa cgcgatgctg gcgtggcagc gcacgcgtt ccacttccag    420 cccccccaaga actggatgaa cggttagttg gacccgtcgc catcggtgac gacgcgcgga    480 tcgtttttttt cttttttcct ctcgttctgg ctctaacttg gttccgcgtt tctgtcacgg    540
acgcctcgtg cacatggcga tacccgatcc gccggccgcg tatatctatc tacctcgacc    600
ggcttctcca gatccgaacg gtaagttgtt ggctccgata cgatcgatca catgtgagct    660
cggcatgctg cttttctgcg cgtgcatgcg gctcctagca ttccacgtcc acgggtcgtg    720
acatcaatgc acgatataat cgtatcggta cagagatatt gtcccatcag ctgctagctt    780
tcgcgtattg atgtcgtgac attttgcacg caggtccgct gtatcacaag gctggtacc    840 acctcttcta ccagtggaac ccggactccg cggtatgggg caacatcacc tggggccacg    900
ccgtctcgcg cgacctcctc cactggctgc acctaccgct ggccatggtg cccgatcacc    960
cgtacgacgc caacggcgtc tggtccgggt cggcgacgcg cctgcccgac ggccggatcg   1020
tcatgctcta cacgggctcc acggcggagt cgtcggcgca ggtgcagaac ctcgcggagc   1080
cggccgacgc gtccgacccg ctgctgcggg agtgggtcaa gtcggacgcc aacccggtgc   1140
tggtgccgcc gccgggcatc gggccgacgg acttccgcga cccgacgacg cgtgtcgga   1200 cgccggccgg caacgacacg gcgtggcggg tcgccatcgg gtccaaggac cgggaccacg   1260

-continued

```
cggggctggc gctggtgtac cggacggagg acttcgtgcg gtacgacccg gcgccggcgc    1320
tgatgcacgc cgtgccgggc accggcatgt gggagtgcgt ggacttctac ccggtggccg    1380
cgggatcagg cgccgcggcg ggcagcgggg acgggctgga gacgtccgcg gcgccgggac    1440
ccggggtgaa gcacgtgctc aaggctagcc tcgacgacga caagcacgac tactacgcga    1500
tcggcaccta cgacccggcg acggacacct ggaccccga cagcgcggag gacgacgtcg    1560
ggatcggcct ccggtacgac tatggcaagt actacgcgtc gaagaccttc tacgaccccg    1620
tccttcgccg gcgggtgctc tggggtggg tcggcgagac cgacagcgag cgcgcggaca    1680
tcctcaaggg ctgggcatcc gtgcaggtac gtctcagggt ttgaggctag catggcttca    1740
atcttgctgg catcgaatca ttaatgggca gatattataa cttgataatc tgggttggtt    1800
gtgtgtggtg gggatggtga cacacgcgcg gtaataatgt agctaagctg gttaaggatg    1860
agtaatgggg ttgcgtataa acgacagctc tgctaccatt acttctgaca cccgattgaa    1920
ggagacaaca gtaggggtag ccggtagggt tcgtcgactt gccttttctt ttttcctttg    1980
ttttgttgtg gatcgtccaa cacaaggaaa ataggatcat ccaacaaaca tggaagtaat    2040
cccgtaaaac atttctcaag gaaccatcta gctagacgag cgtggcatga tccatgcatg    2100
cacaaacact agataggtct ctgcagctgt gatgttcctt tacatatacc accgtccaaa    2160
ctgaatccgg tctgaaaatt gttcaagcag agaggccccg atcctcacac ctgtacacgt    2220
ccctgtacgc gccgtcgtgg tctcccgtga tcctgccccg tcccctccac gcggccacgc    2280
ctgctgcagc gctctgtaca agcgtgcacc acgtgagaat ttccgtctac tcgagcctag    2340
tagttagacg ggaaaacgag aggaagcgca cggtccaagc acaacacttt gcgcgggccc    2400
gtgacttgtc tccggttggc tgagggcgcg cgacagagat gtatggcgcc gcggcgtgtc    2460
ttgtgtcttg tcttgcctat acaccgtagt cagagactgt gtcaaagccg tccaacgaca    2520
atgagctagg aaacggggttg gagagctggg ttcttgcctt gcctcctgtg atgtctttgc    2580
cttgcatagg gggcgcagta tgtagctttg cgttttactt cacgccaaag gatactgctg    2640
atcgtgaatt attattatta tatatatatc gaatatcgat ttcgtcgctc tcgtggggtt    2700
ttattttcca gactcaaact tttcaaaagg cctgtgtttt agttcttttc ttccaattga    2760
gtaggcaagg cgtgtgagtg tgaccaacgc atgcatggat atcgtggtag actggtagag    2820
ctgtcgttac cagcgcgatg cttgtatatg tttgcagtat tttcaaatga atgtctcagc    2880
tagcgtacag ttgaccaagt cgacgtggag ggcgcacaac agacctctga cattattcac    2940
tttttttta ccatgccgtg cacgtgcagt caatccccag gacggtcctc ctggacacga    3000
agacgggcag caacctgctc cagtggccgg tggtggaggt ggagaacctc cggatgagcg    3060
gcaagagctt cgacggcgtc gcgctggacc gcggatccgt cgtgcccctc gacgtcggca    3120
aggcgacgca ggtgacgccg cacgcagcct gctgcagcga acgaactcgc gcgttgccgg    3180
cccgcggcca gctgacttag tttctctggc tgatcgaccg tgtgcctgcg tgcgtgcagt    3240
tggacatcga ggctgtgttc gaggtggacg cgtcggacgc ggcggcgtc acggaggccg    3300
acgtgacgtt caactgcagc accagcgcag gcgcggcggg ccggggcctg ctcggcccgt    3360
tcggccttct cgtgctggcg gacgacgact tgtccgagca gaccgccgtg tacttctacc    3420
tgctcaaggg cacggacggc agcctccaaa ctttcttctg ccaagacgag ctcaggtatg    3480
tatgttatga cttatgacca tgcatgcatg cgcatttctt agctaggctg tgaagcttct    3540
tgttgagttg tttcacagat gcttaccgtc tgctttgttt cgtatttcga ctaggcatcc    3600
aaggcgaacg atctggttaa gagagtatac gggagcttgg tccctgtgct agatggggag    3660
```

```
aatctctcgg tcagaatact ggtaagtttt tacagcgcca gccatgcatg tgttggccag    3720
ccagctgctg gtactttgga cactcgttct tctcgcactg ctcattattg cttctgatct    3780
ggatgcacta caaattgaag gttgaccact ccatcgtgga gagctttgct caaggcggga    3840
ggacgtgcat cacgtcgcga gtgtacccca cacgagccat ctacgactcc gcccgcgtct    3900
tcctcttcaa caacgccaca catgctcacg tcaaagcaaa atccgtcaag atctggcagc    3960
tcaactccgc ctcatccgg ccatatccgg caacgacgac ttctctatga ctaaattaag     4020
tgacggacag ataggcgata ttgcatactt gcatcatgaa ctcatttgta caacagtgat    4080
tgtttaattt atttgctgcc ttccttatcc ttcttgtgaa actatatggt acacacatgt    4140
atcattaggt ctagtagtgt tgttgcaaag acacttagac accagaggtt ccaggagtat    4200
cagagataag gtataagagg gagcagggag cag                                 4233
```

<210> SEQ ID NO 63
<211> LENGTH: 20
<212> TYPE: DNA
<213> ORGANISM: Artificial Sequence
<220> FEATURE:
<223> OTHER INFORMATION: Primer GAAD1-F

<400> SEQUENCE: 63
tgttcggttc cctctaccaa                                                20

<210> SEQ ID NO 64
<211> LENGTH: 22
<212> TYPE: DNA
<213> ORGANISM: Artificial Sequence
<220> FEATURE:
<223> OTHER INFORMATION: Primer GAAD1-R

<400> SEQUENCE: 64
caacatccat caccttgact ga                                             22

<210> SEQ ID NO 65
<211> LENGTH: 24
<212> TYPE: DNA
<213> ORGANISM: Artificial Sequence
<220> FEATURE:
<223> OTHER INFORMATION: Probe GAAD1-P (FAM)

<400> SEQUENCE: 65
cacagaaccg tcgcttcagc aaca                                           24

<210> SEQ ID NO 66
<211> LENGTH: 18
<212> TYPE: DNA
<213> ORGANISM: Artificial Sequence
<220> FEATURE:
<223> OTHER INFORMATION: Primer IVR1-F

<400> SEQUENCE: 66
tggcggacga cgacttgt                                                  18

<210> SEQ ID NO 67
<211> LENGTH: 19
<212> TYPE: DNA
<213> ORGANISM: Artificial Sequence
<220> FEATURE:
<223> OTHER INFORMATION: Primer IVR1-R

<400> SEQUENCE: 67
aaagtttgga ggctgccgt                                              19

<210> SEQ ID NO 68
<211> LENGTH: 26
<212> TYPE: DNA
<213> ORGANISM: Artificial Sequence
<220> FEATURE:
<223> OTHER INFORMATION: Probe IVR1-P (HEX)

<400> SEQUENCE: 68
cgagcagacc gccgtgtact tctacc                                      26

<210> SEQ ID NO 69
<211> LENGTH: 19
<212> TYPE: DNA
<213> ORGANISM: Artificial Sequence
<220> FEATURE:
<223> OTHER INFORMATION: Primer SPC1A

<400> SEQUENCE: 69
cttagctgga taacgccac                                              19

<210> SEQ ID NO 70
<211> LENGTH: 19
<212> TYPE: DNA
<213> ORGANISM: Artificial Sequence
<220> FEATURE:
<223> OTHER INFORMATION: Primer SPC1S

<400> SEQUENCE: 70
gaccgtaagg cttgatgaa                                              19

<210> SEQ ID NO 71
<211> LENGTH: 21
<212> TYPE: DNA
<213> ORGANISM: Artificial Sequence
<220> FEATURE:
<223> OTHER INFORMATION: Probe TQSPEC (CY5*)

<400> SEQUENCE: 71
cgagattctc cgcgctgtag a                                           21

<210> SEQ ID NO 72
<211> LENGTH: 25
<212> TYPE: DNA
<213> ORGANISM: Artificial Sequence
<220> FEATURE:
<223> OTHER INFORMATION: Primer ST-LS1-F

<400> SEQUENCE: 72
gtatgtttct gcttctacct ttgat                                       25

<210> SEQ ID NO 73
<211> LENGTH: 29
<212> TYPE: DNA
<213> ORGANISM: Artificial Sequence
<220> FEATURE:
<223> OTHER INFORMATION: Primer ST-LS1- R

<400> SEQUENCE: 73
ccatgttttg gtcatatatt agaaaagtt                                   29

<210> SEQ ID NO 74
<211> LENGTH: 34
<212> TYPE: DNA
<213> ORGANISM: Artificial Sequence

```
<220> FEATURE:
<223> OTHER INFORMATION: Probe ST-LS1-P (FAM)

<400> SEQUENCE: 74
agtaatatag tatttcaagt attttttttca aaat                             34

<210> SEQ ID NO 75
<211> LENGTH: 20
<212> TYPE: DNA
<213> ORGANISM: Artificial Sequence
<220> FEATURE:
<223> OTHER INFORMATION: Primer Loop_F

<400> SEQUENCE: 75
ggaacgagct gcttgcgtat                                              20

<210> SEQ ID NO 76
<211> LENGTH: 20
<212> TYPE: DNA
<213> ORGANISM: Artificial Sequence
<220> FEATURE:
<223> OTHER INFORMATION: Primer Loop_R

<400> SEQUENCE: 76
cacggtgcag ctgattgatg                                              20

<210> SEQ ID NO 77
<211> LENGTH: 18
<212> TYPE: DNA
<213> ORGANISM: Artificial Sequence
<220> FEATURE:
<223> OTHER INFORMATION: Probe Loop_FAM

<400> SEQUENCE: 77
tcccttccgt agtcagag                                                18

<210> SEQ ID NO 78
<211> LENGTH: 153
<212> TYPE: DNA
<213> ORGANISM: Artificial Sequence
<220> FEATURE:
<223> OTHER INFORMATION: Loop linker polynucleotide

<400> SEQUENCE: 78
agtcatcacg ctggagcgca catataggcc ctccatcaga aagtcattgt gtatatctct   60
catagggaac gagctgcttg cgtatttccc ttccgtagtc agagtcatca atcagctgca  120
ccgtgtcgta aagcgggacg ttcgcaagct cgt                              153

<210> SEQ ID NO 79
<211> LENGTH: 499
<212> TYPE: RNA
<213> ORGANISM: Diabrotica virgifera

<400> SEQUENCE: 79
cgccuuacac uccaaguggu caaacuccau acaugacucc guacgcuaca ccccauacgc   60
agcaaacucc ccgcuauggu caucaaaacac cuucccaaca cauggcgagc ucagcaccac  120
aaggucucaa caaucccuuu uuacauccug gcgcggugac ucccucccaa cgaacuccua  180
uuuaucgcaa ccauccugca caaucuccag uaaugcuucc uacaagcccu guaccaaguc  240 cagguucccca gaguucauac aguagucauu uaagucauaa ucagcgaagu ggaaguuaug  300
cugaauccuu aagauuccaa ccuccccgaau cgccgagaag cucagugagu aauagaagcu  360
```

```
uucaaacuga uagauacggc ggugauaggu augguaaagg aggaagucau agauauggug        420
gaagcucaaa cgaagauaga uaugguaagg gaggaggagg aaaugaaaau acggauuggc        480
agaaagcugc agaagcaug                                                    499

<210> SEQ ID NO 80
<211> LENGTH: 145
<212> TYPE: RNA
<213> ORGANISM: Diabrotica virgifera

<400> SEQUENCE: 80
gacuccguac gcuacacccc auacgcagca aacucccgc uauggucauc aaacaccuuc         60
ccaacacaug gcgagcucag caccacaagg ucucaacaau cccuuuuuac auccuggcgc       120
ggugacuccc ucccaacgaa cuccu                                             145

<210> SEQ ID NO 81
<211> LENGTH: 108
<212> TYPE: RNA
<213> ORGANISM: Diabrotica virgifera

<400> SEQUENCE: 81
agaguucaua caguagucau uuaagucaua aucagcgaag uggaaguuau gcugaauccu        60
uaagauucca accucccgaa ucgccgagaa gcucagugag uaauagaa                    108
```